US012747435B2

(12) United States Patent
Kamon et al.

(10) Patent No.: US 12,747,435 B2
(45) Date of Patent: Sep. 29, 2026

(54) COLLAGENASE AGENT AND USE THEREOF

(71) Applicant: AMANO ENZYME INC., Nagoya (JP)

(72) Inventors: Masahiro Kamon, Kakamigahara (JP); Kensuke Yuki, Kakamigahara (JP); Hiroyuki Yachi, Kakamigahara (JP)

(73) Assignee: AMANO ENZYME INC., Nagoya (JP)

( * ) Notice: Subject to any disclaimer, the term of this patent is extended or adjusted under 35 U.S.C. 154(b) by 600 days.

(21) Appl. No.: 17/915,146

(22) PCT Filed: Mar. 30, 2021

(86) PCT No.: PCT/JP2021/013557
§ 371 (c)(1),
(2) Date: Sep. 28, 2022

(87) PCT Pub. No.: WO2021/200955
PCT Pub. Date: Oct. 7, 2021

(65) Prior Publication Data

US 2023/0114818 A1 Apr. 13, 2023

(30) Foreign Application Priority Data

Mar. 31, 2020 (JP) ................................ 2020-064460

(51) Int. Cl.
*C12N 9/52* (2006.01)
*A23L 13/74* (2023.01)
*C12P 21/06* (2006.01)

(52) U.S. Cl.
CPC ................ *C12N 9/52* (2013.01); *A23L 13/74* (2016.08); *C12P 21/06* (2013.01); *C12Y 304/24003* (2013.01)

(58) Field of Classification Search
CPC .............................................. C12Y 304/24003
See application file for complete search history.

(56) References Cited

U.S. PATENT DOCUMENTS

2016/0339078 A1 11/2016 Hamill et al.
2025/0129353 A1* 4/2025 Kamon .................. A23L 13/48

FOREIGN PATENT DOCUMENTS

CN 103232963 A 8/2013
CN 104017761 A 9/2014
CN 104988127 A 10/2015
CN 106754836 A 5/2017
JP H05-007476 A 1/1993
JP H05-016832 B2 3/1993
JP H08-070853 A 3/1996
JP 2001-037474 A 2/2001
JP 3146251 B2 3/2001
JP 2001-510331 A 7/2001
JP 2002255847 A * 9/2002
JP 2007-246460 A 9/2007
JP 2010-263880 A 11/2010
JP 2018-183106 A 11/2018
JP 6448216 B2 * 1/2019 ..... C12Y 304/24003

OTHER PUBLICATIONS

Unirprot Accession No. A0A1H9AG47, submitted Oct. 2016 Available online at: https://www.uniprot.org/uniprotkb/A0A1H9AG47/entry (Year: 2016).*
Pal, Gaurav Kumar. Fish collagen and microbial collagenase: Production, characterization and their potential food applications. Diss. Ph. D. Thesis, Academy of Scientific & Innovative Research, Ghaziabad, India, 2018. (Year: 2018).*
Ahmed, Iftikhar, et al. "Proposal of *Lysinibacillus boronitolerans* gen. nov. sp. nov . . . " International Journal of Systematic and Evolutionary Microbiology 57.5 (2007): 1117-1125. (Year: 2007).*
Sakurai, Yasuko, et al. "Purification and characterization of a major collagenase from Streptomyces parvulus." Bioscience, biotechnology, and biochemistry 73.1 (2009): 21-28. (Year: 2009).*
Petrova, D., A. Derekova, and S. Vlahov. "Purification and properties of individual collagenases from *Streptomyces* sp. strain 3B." Folia microbiologica 51.2 (2006): 93-98. (Year: 2006).*
Ikeuchi, Takeaki, et al. "Crystal structure of Grimontia hollisae collagenase provides insights into its novel substrate specificity toward collagen." Journal of Biological Chemistry 298.8 (2022). (Year: 2022).*
Office Action dated Jan. 28, 2025 issued in the corresponding Japanese patent application No. 2022-512545 with its English Machine Translation.
"Collagenase [*Lysinibacillus fusiformis*]" Accession No. ODV56102.1, Database GenBank, 2016, 2 pages. (cited in the Jan. 28, 2025 Office Action issued for JP2022-512545).
Y. Sakurai et al., "Purification and Characterization of a Major Collagenase from *Streptomyces parvulus*," Biosci Biotechnol Biochem, vol. 73, 2009, pp. 21-28. (cited in the Jan. 28, 2025 Office Action issued for JP2022-512545).
N. Teramura et al., "Cloning of a Novel Collagenase Gene from the Gram-Negative Bacterium *Grimonita* (*Vibrio*) *hollisae* 1706B and Its Efficient Expression in Brevibacillus choshinensis," Journal of Bacteriology, vol. 193, No. 12, Jun. 2011, pp. 3049-3056. (cited in the Jan. 28, 2025 Office Action issued for JP2022-512545).
U. Eckhard et al., "Structure of collagenase G reveals a chew and digest mechanism of bacterial collagenolysis," Nature Structural & Molecular Biology, vol. 18, No. 10, 2012, pp. 1109-1114. (cited in the Jan. 28, 2025 Office Action issued for JP2022-512545).
Extended European Search Report dated Apr. 3, 2024, issued in the corresponding European patent application No. 21782351.7.

(Continued)

*Primary Examiner* — Robert J Yamasaki
(74) *Attorney, Agent, or Firm* — Troutman Pepper Locke LLP

(57) ABSTRACT

The object of the present invention is to provide highly safe collagenase that is useful for food or medical use, and the use thereof. Provided is an enzyme agent comprising, as an active ingredient, collagenase having an amino acid sequence having an identity of 90% or more to the amino acid sequence as set forth in SEQ ID NO: 1. This enzyme agent is useful for production of a collagen tripeptide or tenderization of edible meat.

5 Claims, 9 Drawing Sheets

Specification includes a Sequence Listing.

(56) References Cited

OTHER PUBLICATIONS

International Search Report and Written Opinion mailed May 11, 2021, issued for PCT/JP2021/013557.

International Preliminary Report on Patentability of Chapter I dated Sep. 29, 2022, issued for PCT/JP2021/013557 and English translation thereof.

Accession No. A0A410MLN5, May 8, 2019, 1 page. (cited in the ISR).

Accession No. A0A1E4R6K6, Jan. 18, 2017, 1 page. (cited in the ISR).

Accession No. A0A1H8BD11, Nov. 22, 2017, 1 page. (cited in the ISR).

Accession No. A0A0B1XVT2, Mar. 4, 2015, 1 page. (cited in the ISR).

Accession No. B1HXW1, Apr. 29, 2008, 1 page. (cited in the ISR).

Accession No. W7SCF9, Apr. 16, 2014. (cited in the ISR).

Office Action dated Aug. 28, 2024, issued in the corresponding Chinese patent application No. 202180025486.2 with its English Machine Translation.

"PKD domain-containing protein [*Lysinibacillus fusiformis*]", WP-096364288.1, GenBank, 2020, 2 pages. (cited in the Aug. 28, 2024 Office Action issued for CN02180025486.2).

Sneha B. Sontakke et al., "Orally Available Collagen Tripeptide: Enzymatic Stability, Intestinal Permeability, and Absorption of Gly-Pro-Hyp and Pro-Hyp," J. Agric. Food Chem., vol. 64, 2016, pp. 7127-7133. (cited in the Aug. 28, 2024 Office Action issued for CN02180025486.2).

Li Ya-nan et al., "Bioactivities and applications of collagen tripeptides: A review", Science and Technology of Food Industry, vol. 39, No. 3, 2018, pp. 333-337 and English abstract thereof. (cited in the Aug. 28, 2024 Office Action issued for CN02180025486.2).

Office Action dated Mar. 7, 2025, issued in the corresponding Chinese patent application No. 202180025486.2 with its English Machine Translation.

Office Action dated Apr. 8, 2025, issued in the corresponding Japanese patent application No. 2022-512545 with its English Machine Translation.

Office Action dated May 30, 2025, issued in the corresponding Chinese patent application No. 202180025486.2 with its English Machine Translation.

Office Action dated May 19, 2026, issued in the corresponding Japanese patent application No. JP2025-093794 with its English Machine Translation.

* cited by examiner

[Fig. 1]

MKKKFTFNQLLIGVSTMAISLGGLQAEASAAEKTPYNVLQMKPIGIEMSKDEMVHSTMAEE
TLSYEERLEMGDFSQRPAPIMEQMDTQQLQEQYSMAELNNMSNRELIHTLGSIRWYQITDLF
QFNDDTKAFYQNEERMQVIINELGNRGNSFTKEDSKGIETFVEVLRSAFYVAFYNNELGYLN
ERSFQDKCLPALNEIAKNPNFKLGTDEQDKVVSAYGKLIGNASSDVETVQHATNILKQYNEN
LSTYESENSKGQAIYDIIHGIDYDLQSYLYDTRKEANTTMWYGKIDSFIEEVNNIALIHNVTD
SNSWLINNGIYYAGRLGQFHSNPNKGLEVVTQAMHMYPYLSEAYFVAVEQITTNYGGRDLN
GNTVDLQKVREEGKKQYLPKTYTFDDGSIVFKTGDQVTEDKIQRLYWAAKEVKAQYHRVI
GNDQALEPGNADDILTVVIYNSPDQYRLNRQLYGYETNNGGIYIEETGTFFTYERTPEQSIYS
LEELFRHEYTHFLQGRFEVPGLFGTGDMYQNERLTWFQEGNAEFFAGSTRTNDVVPRKSIIS
GLSQDPSQRYTAEQTMFATYGSWDFYNYSFALQSYMYTHQFDMFDRIQDLIRANDVKNYD
AYRDTLSKDSQLNMEYQAYMQQLIDNQETYEVPQVAEDYLMPHEPKALNEVQQEIVDIAH
VKDANMTKHQSQFFNTFTLEGTYVGSATQGESQDWKTMSKQVNQMLEQLSQKEWSGYKT
MTAYFVNYRVNAANQFEYDVVFHGVSTDDGETQAPIVQVNGPYTGMINEKIQFNSDGSKD
TDGEIVSYLWDFGDGATSEAANPTHVYENEGTYKVTLTVKNNKGQESKGQTTATVQKGGQ
TGQEHAMIIPFNKPLKGSLIENDTNVYQFDITSPEEIDISVVNENQIGMTWVLYHESDKENYV
AYGQEDGQTIKGKYNAKPGKYYLYVYKFDDEDGTYTVQVQNSTKTEIEPNNRPEEATMLPF
HTPLSGSLMEDDHTDVYEFNVTSPKEIDISVLNENQIGMTWVLYHESDSQNYASFGQEDGN
MINGKLNAKPGKYYLYVYKFENENGTYTVHVQ (SEQ ID NO: 2)

[Fig. 2]
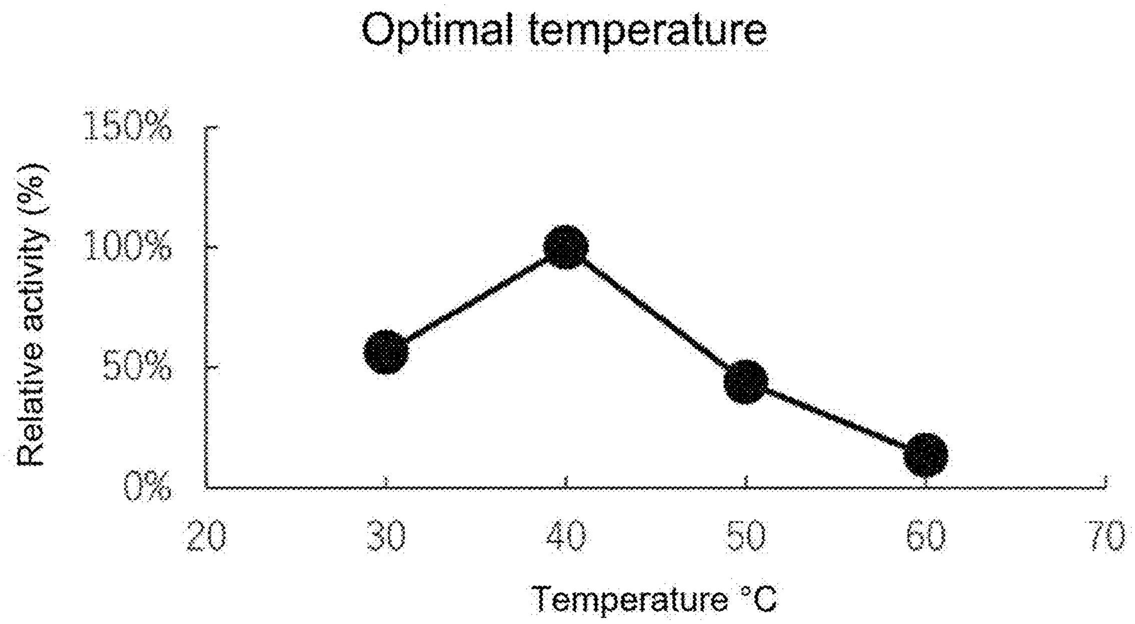
[Fig. 3]
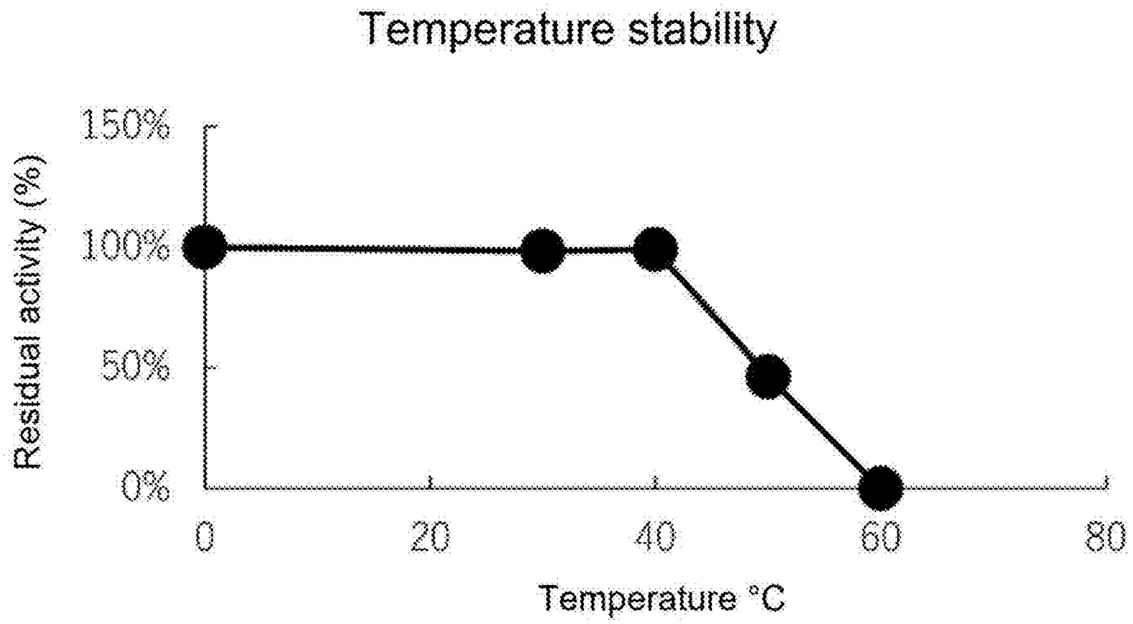

[Fig. 4]
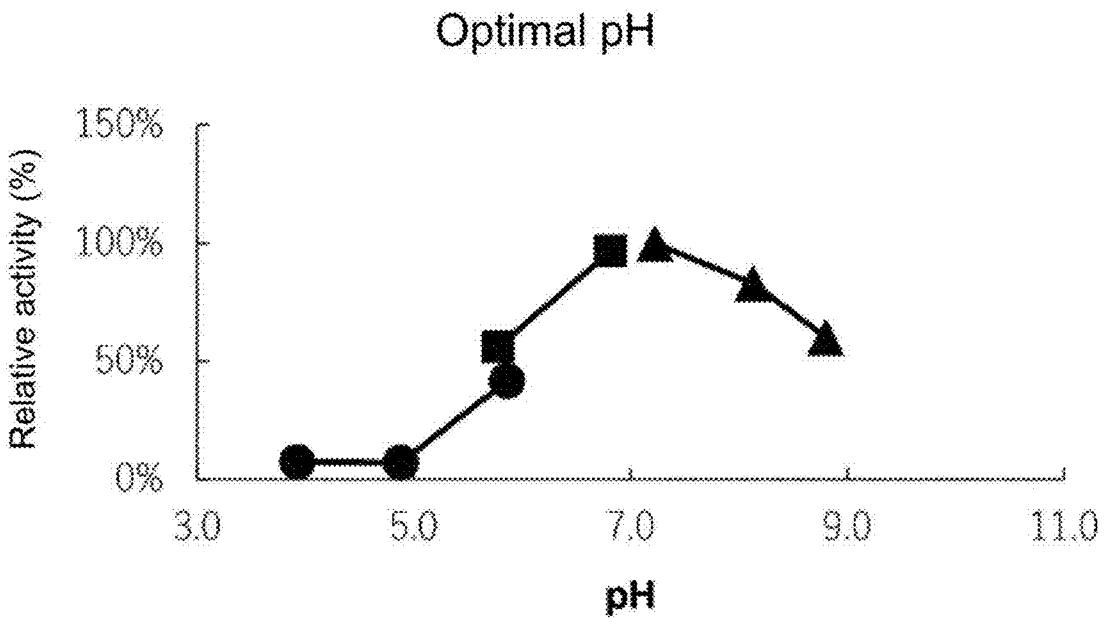
[Fig. 5]
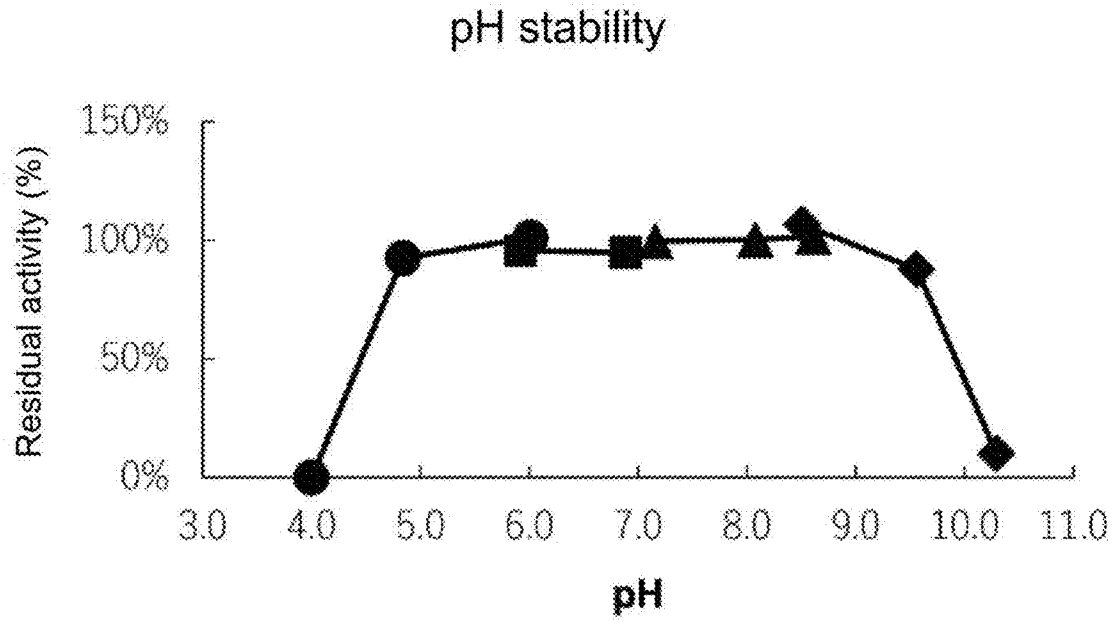

[Fig. 6]
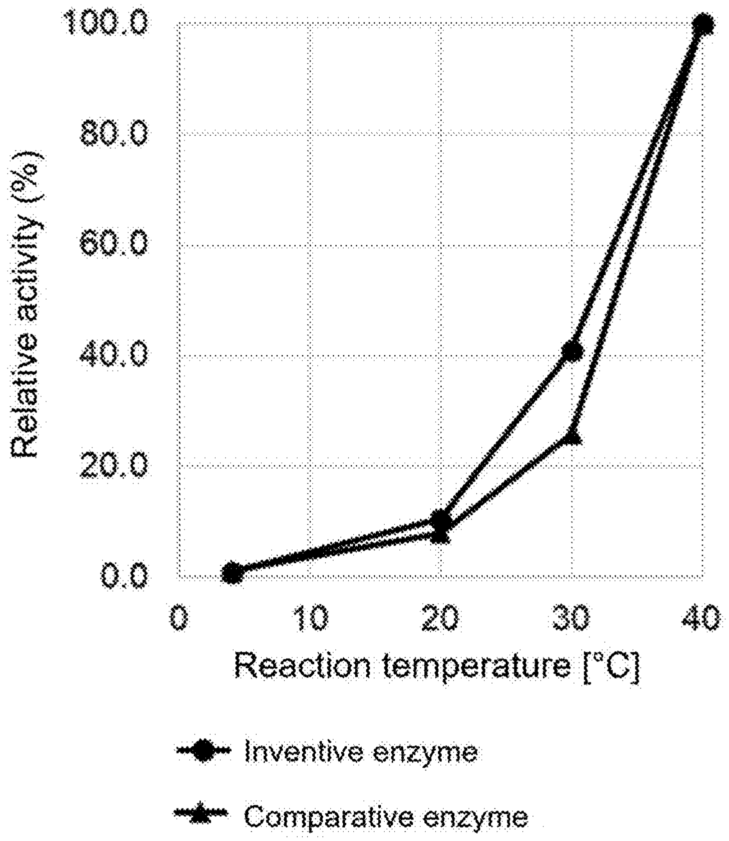

[Fig. 7]
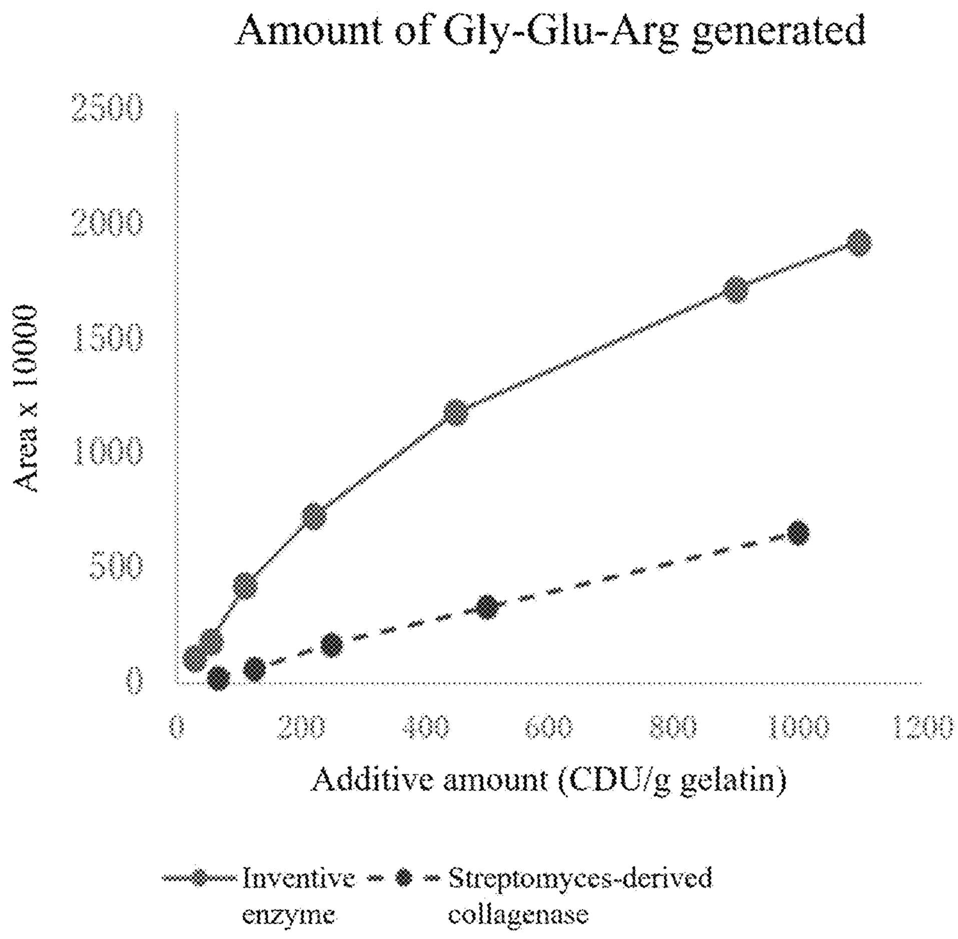

[Fig. 8]
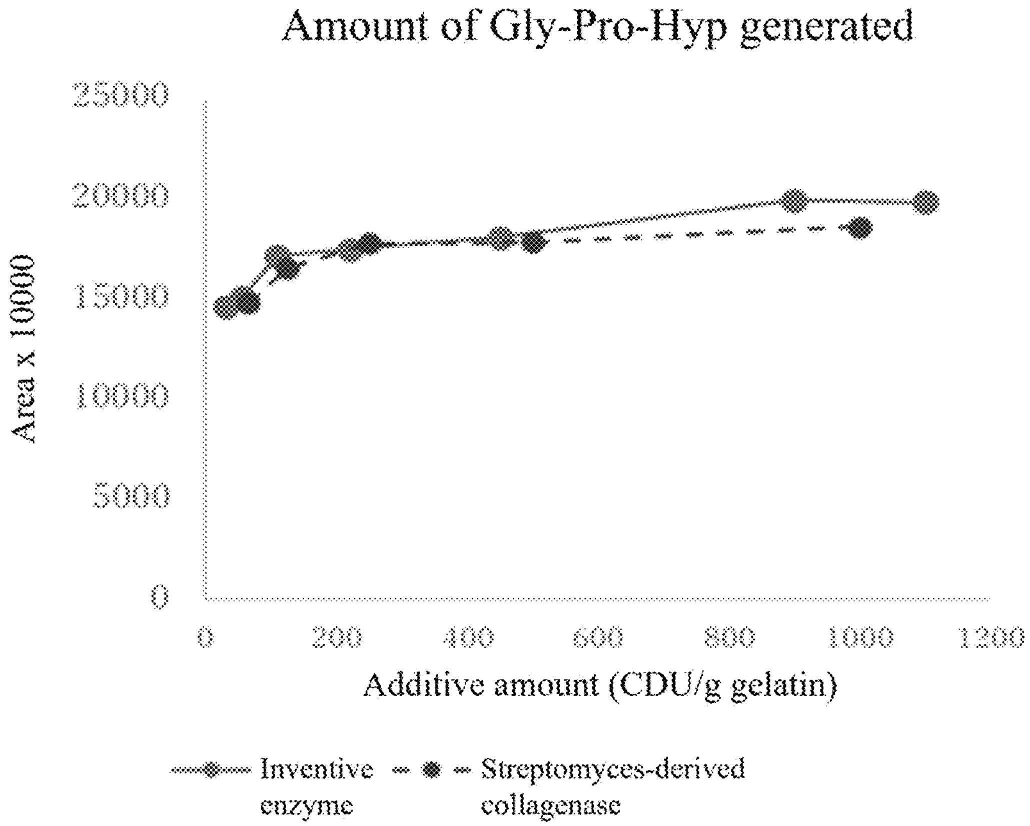

[Fig. 9]
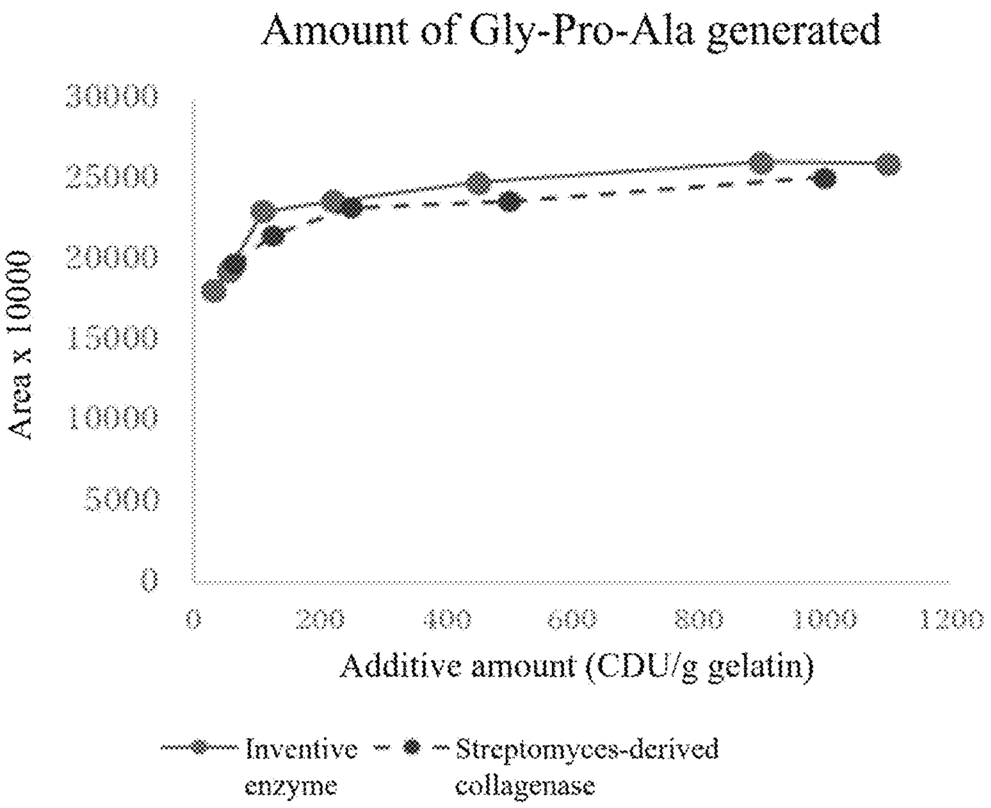

[Fig. 10]
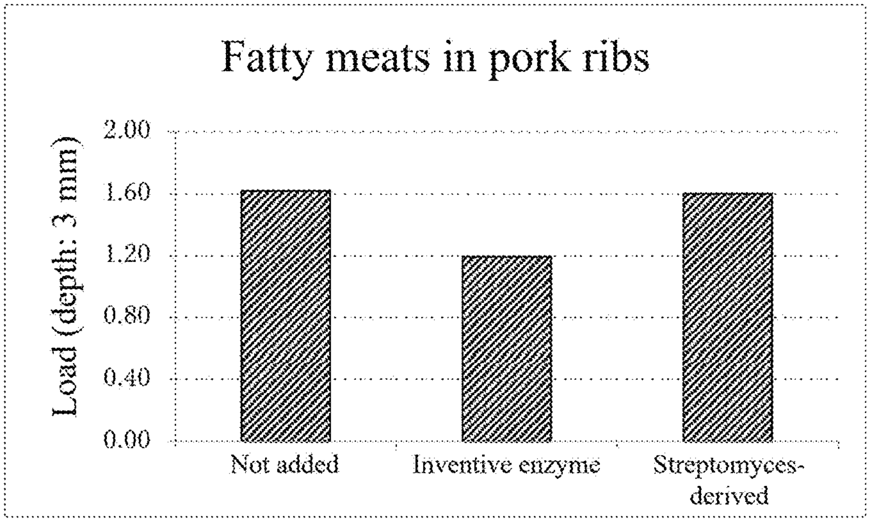
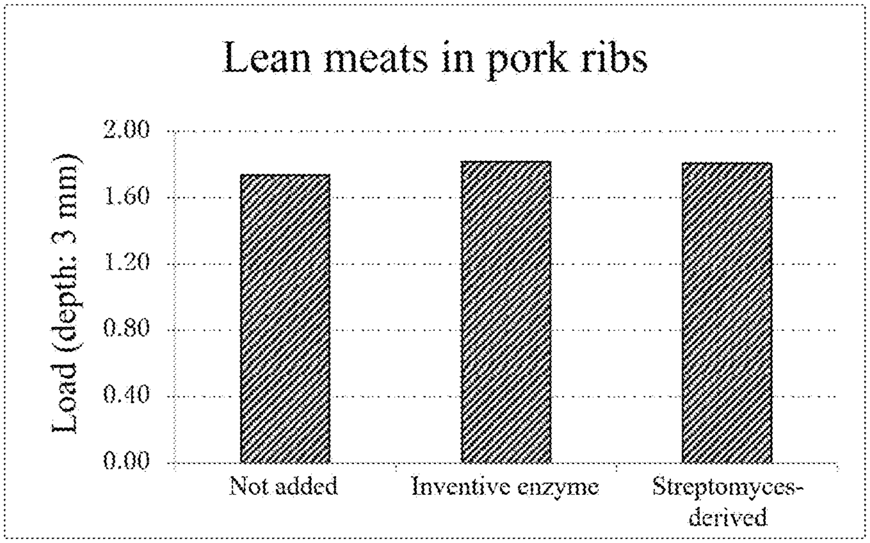

[Fig. 11]
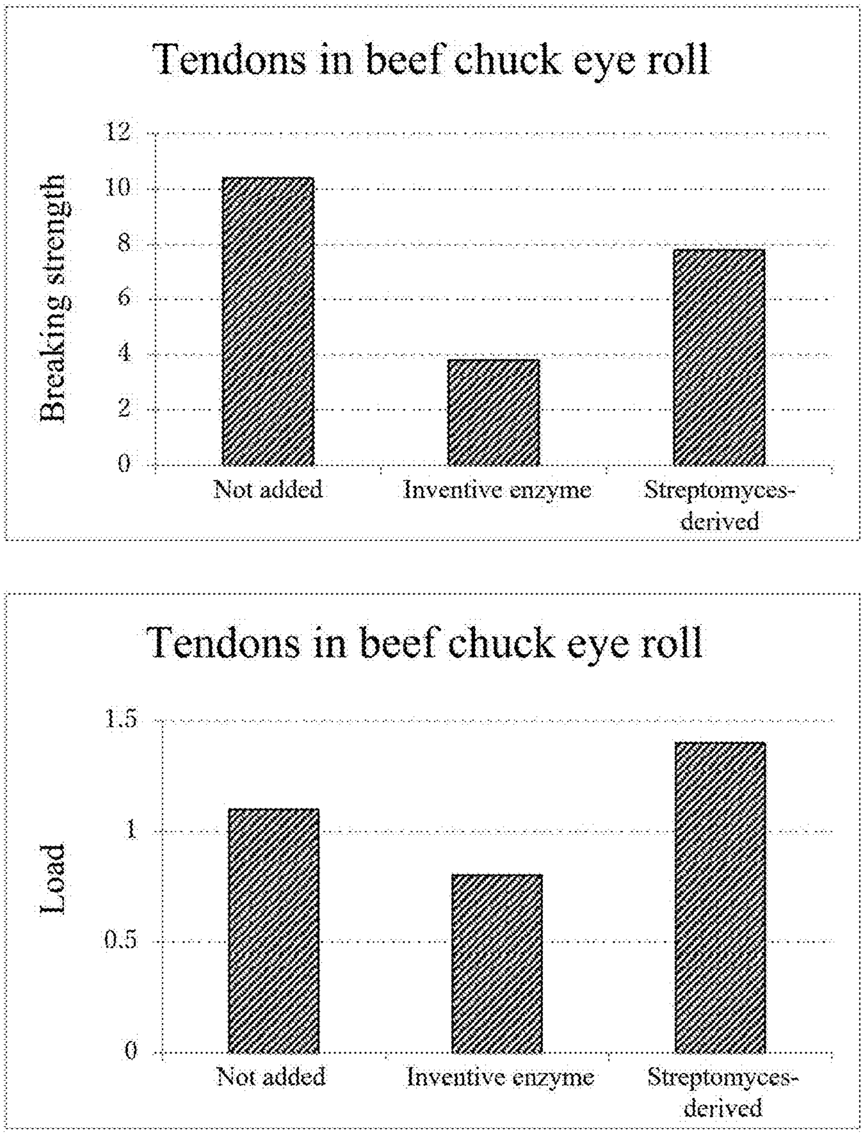

SEQUENCE LISTING

```
<160> NUMBER OF SEQ ID NOS: 6

<210> SEQ ID NO 1
<211> LENGTH: 987
<212> TYPE: PRT
<213> ORGANISM: Lysinibacillus fusiformis

<400> SEQUENCE: 1

Asp Thr Gln Gln Leu Gln Glu Gln Tyr Ser Met Ala Glu Leu Asn Asn
1               5                   10                  15

Met Ser Asn Arg Glu Leu Ile His Thr Leu Gly Ser Ile Arg Trp Tyr
            20                  25                  30

Gln Ile Thr Asp Leu Phe Gln Phe Asn Asp Asp Thr Lys Ala Phe Tyr
        35                  40                  45

Gln Asn Glu Glu Arg Met Gln Val Ile Ile Asn Glu Leu Gly Asn Arg
    50                  55                  60
```

-continued

```
Gly Asn Ser Phe Thr Lys Glu Asp Ser Lys Gly Ile Glu Thr Phe Val
65                  70                  75                  80

Glu Val Leu Arg Ser Ala Phe Tyr Val Ala Phe Tyr Asn Asn Glu Leu
                85                  90                  95

Gly Tyr Leu Asn Glu Arg Ser Phe Gln Asp Lys Cys Leu Pro Ala Leu
            100                 105                 110

Asn Glu Ile Ala Lys Asn Pro Asn Phe Lys Leu Gly Thr Asp Glu Gln
        115                 120                 125

Asp Lys Val Val Ser Ala Tyr Gly Lys Leu Ile Gly Asn Ala Ser Ser
    130                 135                 140

Asp Val Glu Thr Val Gln His Ala Thr Asn Ile Leu Lys Gln Tyr Asn
145                 150                 155                 160

Glu Asn Leu Ser Thr Tyr Glu Ser Glu Asn Ser Lys Gly Gln Ala Ile
                165                 170                 175

Tyr Asp Ile Ile His Gly Ile Asp Tyr Asp Leu Gln Ser Tyr Leu Tyr
            180                 185                 190

Asp Thr Arg Lys Glu Ala Asn Thr Thr Met Trp Tyr Gly Lys Ile Asp
        195                 200                 205

Ser Phe Ile Glu Glu Val Asn Asn Ile Ala Leu Ile His Asn Val Thr
    210                 215                 220

Asp Ser Asn Ser Trp Leu Ile Asn Asn Gly Ile Tyr Tyr Ala Gly Arg
225                 230                 235                 240

Leu Gly Gln Phe His Ser Asn Pro Asn Lys Gly Leu Glu Val Val Thr
                245                 250                 255

Gln Ala Met His Met Tyr Pro Tyr Leu Ser Glu Ala Tyr Phe Val Ala
            260                 265                 270

Val Glu Gln Ile Thr Thr Asn Tyr Gly Gly Arg Asp Leu Asn Gly Asn
        275                 280                 285

Thr Val Asp Leu Gln Lys Val Arg Glu Glu Gly Lys Lys Gln Tyr Leu
    290                 295                 300

Pro Lys Thr Tyr Thr Phe Asp Asp Gly Ser Ile Val Phe Lys Thr Gly
305                 310                 315                 320

Asp Gln Val Thr Glu Asp Lys Ile Gln Arg Leu Tyr Trp Ala Ala Lys
                325                 330                 335

Glu Val Lys Ala Gln Tyr His Arg Val Ile Gly Asn Asp Gln Ala Leu
            340                 345                 350

Glu Pro Gly Asn Ala Asp Asp Ile Leu Thr Val Val Ile Tyr Asn Ser
        355                 360                 365

Pro Asp Gln Tyr Arg Leu Asn Arg Gln Leu Tyr Gly Tyr Glu Thr Asn
    370                 375                 380

Asn Gly Gly Ile Tyr Ile Glu Glu Thr Gly Thr Phe Phe Thr Tyr Glu
385                 390                 395                 400

Arg Thr Pro Glu Gln Ser Ile Tyr Ser Leu Glu Glu Leu Phe Arg His
                405                 410                 415

Glu Tyr Thr His Phe Leu Gln Gly Arg Phe Glu Val Pro Gly Leu Phe
            420                 425                 430

Gly Thr Gly Asp Met Tyr Gln Asn Glu Arg Leu Thr Trp Phe Gln Glu
        435                 440                 445

Gly Asn Ala Glu Phe Phe Ala Gly Ser Thr Arg Thr Asn Asp Val Val
    450                 455                 460

Pro Arg Lys Ser Ile Ile Ser Gly Leu Ser Gln Asp Pro Ser Gln Arg
465                 470                 475                 480

Tyr Thr Ala Glu Gln Thr Met Phe Ala Thr Tyr Gly Ser Trp Asp Phe
```

```
                485                 490                 495

Tyr Asn Tyr Ser Phe Ala Leu Gln Ser Tyr Met Tyr Thr His Gln Phe
            500                 505                 510

Asp Met Phe Asp Arg Ile Gln Asp Leu Ile Arg Ala Asn Asp Val Lys
        515                 520                 525

Asn Tyr Asp Ala Tyr Arg Asp Thr Leu Ser Lys Asp Ser Gln Leu Asn
    530                 535                 540

Met Glu Tyr Gln Ala Tyr Met Gln Gln Leu Ile Asp Asn Gln Glu Thr
545                 550                 555                 560

Tyr Glu Val Pro Gln Val Ala Glu Asp Tyr Leu Met Pro His Glu Pro
                565                 570                 575

Lys Ala Leu Asn Glu Val Gln Gln Glu Ile Val Asp Ile Ala His Val
            580                 585                 590

Lys Asp Ala Asn Met Thr Lys His Gln Ser Gln Phe Phe Asn Thr Phe
        595                 600                 605

Thr Leu Glu Gly Thr Tyr Val Gly Ser Ala Thr Gln Gly Glu Ser Gln
    610                 615                 620

Asp Trp Lys Thr Met Ser Lys Gln Val Asn Gln Met Leu Glu Gln Leu
625                 630                 635                 640

Ser Gln Lys Glu Trp Ser Gly Tyr Lys Thr Met Thr Ala Tyr Phe Val
                645                 650                 655

Asn Tyr Arg Val Asn Ala Ala Asn Gln Phe Glu Tyr Asp Val Val Phe
            660                 665                 670

His Gly Val Ser Thr Asp Asp Gly Glu Thr Gln Ala Pro Ile Val Gln
        675                 680                 685

Val Asn Gly Pro Tyr Thr Gly Met Ile Asn Glu Lys Ile Gln Phe Asn
    690                 695                 700

Ser Asp Gly Ser Lys Asp Thr Asp Gly Glu Ile Val Ser Tyr Leu Trp
705                 710                 715                 720

Asp Phe Gly Asp Gly Ala Thr Ser Glu Ala Ala Asn Pro Thr His Val
                725                 730                 735

Tyr Glu Asn Glu Gly Thr Tyr Lys Val Thr Leu Thr Val Lys Asn Asn
            740                 745                 750

Lys Gly Gln Glu Ser Lys Gly Gln Thr Thr Ala Thr Val Gln Lys Gly
        755                 760                 765

Gly Gln Thr Gly Gln Glu His Ala Met Ile Ile Pro Phe Asn Lys Pro
    770                 775                 780

Leu Lys Gly Ser Leu Ile Glu Asn Asp Thr Asn Val Tyr Gln Phe Asp
785                 790                 795                 800

Ile Thr Ser Pro Glu Glu Ile Asp Ile Ser Val Val Asn Glu Asn Gln
                805                 810                 815

Ile Gly Met Thr Trp Val Leu Tyr His Glu Ser Asp Lys Glu Asn Tyr
            820                 825                 830

Val Ala Tyr Gly Gln Glu Asp Gly Gln Thr Ile Lys Gly Lys Tyr Asn
        835                 840                 845

Ala Lys Pro Gly Lys Tyr Tyr Leu Tyr Val Tyr Lys Phe Asp Asp Glu
    850                 855                 860

Asp Gly Thr Tyr Thr Val Gln Val Gln Asn Ser Thr Lys Thr Glu Ile
865                 870                 875                 880

Glu Pro Asn Asn Arg Pro Glu Glu Ala Thr Met Leu Pro Phe His Thr
                885                 890                 895

Pro Leu Ser Gly Ser Leu Met Glu Asp Asp His Thr Asp Val Tyr Glu
            900                 905                 910
```

```
Phe Asn Val Thr Ser Pro Lys Glu Ile Asp Ile Ser Val Leu Asn Glu
        915                 920                 925

Asn Gln Ile Gly Met Thr Trp Val Leu Tyr His Glu Ser Asp Ser Gln
    930                 935                 940

Asn Tyr Ala Ser Phe Gly Gln Glu Asp Gly Asn Met Ile Asn Gly Lys
945                 950                 955                 960

Leu Asn Ala Lys Pro Gly Lys Tyr Tyr Leu Tyr Val Tyr Lys Phe Glu
                965                 970                 975

Asn Glu Asn Gly Thr Tyr Thr Val His Val Gln
            980                 985


<210> SEQ ID NO 2
<211> LENGTH: 1072
<212> TYPE: PRT
<213> ORGANISM: Lysinibacillus fusiformis

<400> SEQUENCE: 2

Met Lys Lys Lys Phe Thr Phe Asn Gln Leu Leu Ile Gly Val Ser Thr
1               5                   10                  15

Met Ala Ile Ser Leu Gly Gly Leu Gln Ala Glu Ala Ser Ala Ala Glu
            20                  25                  30

Lys Thr Pro Tyr Asn Val Leu Gln Met Lys Pro Ile Gly Ile Glu Met
        35                  40                  45

Ser Lys Asp Glu Met Val His Ser Thr Met Ala Glu Glu Thr Leu Ser
    50                  55                  60

Tyr Glu Glu Arg Leu Glu Met Gly Asp Phe Ser Gln Arg Pro Ala Pro
65                  70                  75                  80

Ile Met Glu Gln Met Asp Thr Gln Gln Leu Gln Glu Gln Tyr Ser Met
                85                  90                  95

Ala Glu Leu Asn Asn Met Ser Asn Arg Glu Leu Ile His Thr Leu Gly
            100                 105                 110

Ser Ile Arg Trp Tyr Gln Ile Thr Asp Leu Phe Gln Phe Asn Asp Asp
        115                 120                 125

Thr Lys Ala Phe Tyr Gln Asn Glu Glu Arg Met Gln Val Ile Ile Asn
    130                 135                 140

Glu Leu Gly Asn Arg Gly Asn Ser Phe Thr Lys Glu Asp Ser Lys Gly
145                 150                 155                 160

Ile Glu Thr Phe Val Glu Val Leu Arg Ser Ala Phe Tyr Val Ala Phe
                165                 170                 175

Tyr Asn Asn Glu Leu Gly Tyr Leu Asn Glu Arg Ser Phe Gln Asp Lys
            180                 185                 190

Cys Leu Pro Ala Leu Asn Glu Ile Ala Lys Asn Pro Asn Phe Lys Leu
        195                 200                 205

Gly Thr Asp Glu Gln Asp Lys Val Val Ser Ala Tyr Gly Lys Leu Ile
    210                 215                 220

Gly Asn Ala Ser Ser Asp Val Glu Thr Val Gln His Ala Thr Asn Ile
225                 230                 235                 240

Leu Lys Gln Tyr Asn Glu Asn Leu Ser Thr Tyr Glu Ser Glu Asn Ser
                245                 250                 255

Lys Gly Gln Ala Ile Tyr Asp Ile Ile His Gly Ile Asp Tyr Asp Leu
            260                 265                 270

Gln Ser Tyr Leu Tyr Asp Thr Arg Lys Glu Ala Asn Thr Thr Met Trp
        275                 280                 285

Tyr Gly Lys Ile Asp Ser Phe Ile Glu Glu Val Asn Asn Ile Ala Leu
```

-continued

```
    290                 295                 300

Ile His Asn Val Thr Asp Ser Asn Ser Trp Leu Ile Asn Asn Gly Ile
305                 310                 315                 320

Tyr Tyr Ala Gly Arg Leu Gly Gln Phe His Ser Asn Pro Asn Lys Gly
                325                 330                 335

Leu Glu Val Val Thr Gln Ala Met His Met Tyr Pro Tyr Leu Ser Glu
            340                 345                 350

Ala Tyr Phe Val Ala Val Glu Gln Ile Thr Thr Asn Tyr Gly Gly Arg
        355                 360                 365

Asp Leu Asn Gly Asn Thr Val Asp Leu Gln Lys Val Arg Glu Glu Gly
    370                 375                 380

Lys Lys Gln Tyr Leu Pro Lys Thr Tyr Thr Phe Asp Asp Gly Ser Ile
385                 390                 395                 400

Val Phe Lys Thr Gly Asp Gln Val Thr Glu Asp Lys Ile Gln Arg Leu
                405                 410                 415

Tyr Trp Ala Ala Lys Glu Val Lys Ala Gln Tyr His Arg Val Ile Gly
            420                 425                 430

Asn Asp Gln Ala Leu Glu Pro Gly Asn Ala Asp Asp Ile Leu Thr Val
        435                 440                  445

Val Ile Tyr Asn Ser Pro Asp Gln Tyr Arg Leu Asn Arg Gln Leu Tyr
    450                 455                 460

Gly Tyr Glu Thr Asn Asn Gly Gly Ile Tyr Ile Glu Glu Thr Gly Thr
465                 470                 475                 480

Phe Phe Thr Tyr Glu Arg Thr Pro Glu Gln Ser Ile Tyr Ser Leu Glu
                485                 490                  495

Glu Leu Phe Arg His Glu Tyr Thr His Phe Leu Gln Gly Arg Phe Glu
            500                 505                 510

Val Pro Gly Leu Phe Gly Thr Gly Asp Met Tyr Gln Asn Glu Arg Leu
        515                 520                 525

Thr Trp Phe Gln Glu Gly Asn Ala Glu Phe Phe Ala Gly Ser Thr Arg
    530                 535                 540

Thr Asn Asp Val Val Pro Arg Lys Ser Ile Ile Ser Gly Leu Ser Gln
545                 550                 555                 560

Asp Pro Ser Gln Arg Tyr Thr Ala Glu Gln Thr Met Phe Ala Thr Tyr
                565                 570                 575

Gly Ser Trp Asp Phe Tyr Asn Tyr Ser Phe Ala Leu Gln Ser Tyr Met
            580                 585                 590

Tyr Thr His Gln Phe Asp Met Phe Asp Arg Ile Gln Asp Leu Ile Arg
        595                 600                 605

Ala Asn Asp Val Lys Asn Tyr Asp Ala Tyr Arg Asp Thr Leu Ser Lys
    610                 615                 620

Asp Ser Gln Leu Asn Met Glu Tyr Gln Ala Tyr Met Gln Gln Leu Ile
625                 630                 635                 640

Asp Asn Gln Glu Thr Tyr Glu Val Pro Gln Val Ala Glu Asp Tyr Leu
                645                 650                 655

Met Pro His Glu Pro Lys Ala Leu Asn Glu Val Gln Gln Glu Ile Val
            660                 665                 670

Asp Ile Ala His Val Lys Asp Ala Asn Met Thr Lys His Gln Ser Gln
        675                 680                 685

Phe Phe Asn Thr Phe Thr Leu Glu Gly Thr Tyr Val Gly Ser Ala Thr
    690                 695                 700

Gln Gly Glu Ser Gln Asp Trp Lys Thr Met Ser Lys Gln Val Asn Gln
705                 710                 715                 720
```

```
Met Leu Glu Gln Leu Ser Gln Lys Glu Trp Ser Gly Tyr Lys Thr Met
                725                 730                 735

Thr Ala Tyr Phe Val Asn Tyr Arg Val Asn Ala Ala Asn Gln Phe Glu
            740                 745                 750

Tyr Asp Val Val Phe His Gly Val Ser Thr Asp Asp Gly Glu Thr Gln
        755                 760                 765

Ala Pro Ile Val Gln Val Asn Gly Pro Tyr Thr Gly Met Ile Asn Glu
    770                 775                 780

Lys Ile Gln Phe Asn Ser Asp Gly Ser Lys Asp Thr Asp Gly Glu Ile
785                 790                 795                 800

Val Ser Tyr Leu Trp Asp Phe Gly Asp Gly Ala Thr Ser Glu Ala Ala
                805                 810                 815

Asn Pro Thr His Val Tyr Glu Asn Glu Gly Thr Tyr Lys Val Thr Leu
            820                 825                 830

Thr Val Lys Asn Asn Lys Gly Gln Glu Ser Lys Gly Gln Thr Thr Ala
        835                 840                 845

Thr Val Gln Lys Gly Gly Gln Thr Gly Gln Glu His Ala Met Ile Ile
    850                 855                 860

Pro Phe Asn Lys Pro Leu Lys Gly Ser Leu Ile Glu Asn Asp Thr Asn
865                 870                 875                 880

Val Tyr Gln Phe Asp Ile Thr Ser Pro Glu Glu Ile Asp Ile Ser Val
                885                 890                 895

Val Asn Glu Asn Gln Ile Gly Met Thr Trp Val Leu Tyr His Glu Ser
            900                 905                 910

Asp Lys Glu Asn Tyr Val Ala Tyr Gly Gln Glu Asp Gly Gln Thr Ile
        915                 920                 925

Lys Gly Lys Tyr Asn Ala Lys Pro Gly Lys Tyr Tyr Leu Tyr Val Tyr
    930                 935                 940

Lys Phe Asp Asp Glu Asp Gly Thr Tyr Thr Val Gln Val Gln Asn Ser
945                 950                 955                 960

Thr Lys Thr Glu Ile Glu Pro Asn Asn Arg Pro Glu Glu Ala Thr Met
                965                 970                 975

Leu Pro Phe His Thr Pro Leu Ser Gly Ser Leu Met Glu Asp Asp His
            980                 985                 990

Thr Asp Val Tyr Glu Phe Asn Val Thr Ser Pro Lys Glu Ile Asp Ile
        995                 1000                1005

Ser Val Leu Asn Glu Asn Gln Ile Gly Met Thr Trp Val Leu Tyr
    1010                1015                1020

His Glu Ser Asp Ser Gln Asn Tyr Ala Ser Phe Gly Gln Glu Asp
    1025                1030                1035

Gly Asn Met Ile Asn Gly Lys Leu Asn Ala Lys Pro Gly Lys Tyr
    1040                1045                1050

Tyr Leu Tyr Val Tyr Lys Phe Glu Asn Glu Asn Gly Thr Tyr Thr
    1055                1060                1065

Val His Val Gln
    1070
```

<210> SEQ ID NO 3
<211> LENGTH: 2964
<212> TYPE: DNA
<213> ORGANISM: Lysinibacillus fusiformis

<400> SEQUENCE: 3

```
gatacacagc aattgcagga gcagtactcg atggcagagc ttaataatat gagcaatcgt      60
```

-continued

```
gagcttatcc atacgcttgg cagtatccgt tggtaccaaa ttacagactt attccaattc    120
aatgatgaca caaaagcttt ttatcaaaat gaagagcgca tgcaagtaat catcaatgaa    180
ttagggaata gaggaaattc gtttacgaag gaagattcaa aggggatcga aacatttgtt    240
gaggtattgc gttctgcttt ttatgtagcg ttttataata atgaactagg ctatttaaat    300
gagagaagtt tccaagataa gtgtttacca gcattaaatg aaatagccaa aaatccaaac    360
tttaaacttg gtacagatga gcaagataaa gttgtatctg cctatggaaa attaataggt    420
aatgcttcta gtgatgtgga aaccgttcaa catgctacga acattttaaa acaatataat    480
gaaaatcttt ctacctatga aagtgagaat tcaaaaggac aagctattta cgatataata    540
cacggcattg attatgattt gcagtcttat ttatatgaca ctcgtaaaga ggccaataca    600
acgatgtggt atgggaagat tgatagcttc atagaggaag ttaataacat tgccctaata    660
cataatgtga cggatagcaa tagttggtta attaataatg gcatttatta tgcagggcgt    720
ttagggcagt tccatagcaa tcctaataag ggtttagaag tcgttacaca agcgatgcat    780
atgtatccct atttaagtga agcttatttt gtggcagtag agcaaattac gacaaattat    840
ggtggacgtg acttaaacgg aaatacggtt gatttacaaa aagtacgtga agaaggaaaa    900
aaacagtatc taccgaaaac atatacattt gatgatggat caattgtatt caaaacggga    960
gatcaagtaa cggaagataa aattcaaaga ttatactggg ctgcaaaaga ggtaaaggca   1020
caatatcatc gtgtaatcgg gaatgatcaa gcactagagc ctggtaatgc tgacgatatc   1080
ttaaccgttg tcatttataa ctctcccgat cagtaccgat taaaccgaca attgtacgga   1140
tatgaaacaa ataatggtgg tatttatatt gaagagactg gaacattctt tacatatgaa   1200
cgtacacctg agcaaagtat ttatagctta gaagagctgt tccgtcatga atatacgcac   1260
tttttacaag gtagatttga ggtgcctggt ctattcggga cgggtgatat gtatcaaaat   1320
gagcgactaa catggttcca ggaagggaat gcagaatttt ttgcagggtc aacacgtaca   1380
aatgacgttg tgcctcgtaa gagcattatt agtggattgt cacaggatcc atcacaacgc   1440
tatactgctg aacaaacaat gtttgccaca tatggttcct gggattttta taattattca   1500
tttgcattac agtcttatat gtatacgcat caattcgata tgtttgatag aattcaagat   1560
ttaatccgcg cgaacgatgt gaaaaattat gatgcctatc gtgacacttt aagtaaagat   1620
tcacagctga atatggaata ccaagcatat atgcagcaat tgatcgataa ccaagaaaca   1680
tacgaagtac cacaagtagc agaggattat ttaatgccgc atgaaccaaa agcgttaaac   1740
gaagtacagc aagaaattgt cgatattgca catgtgaaag atgcaaatat gacgaaacac   1800
cagtctcaat tttttaatac gtttacactc gagggaacat atgtaggtag tgcaacacag   1860
ggtgaatctc aagattggaa aacgatgagt aagcaagtaa accaaatgct ggagcaactg   1920
tctcaaaaag agtggagcgg ctataaaaca atgactgcgt actttgtcaa ctatcgtgta   1980
aatgcggcaa accagttcga gtatgatgta gtcttccatg gcgtttccac tgatgacgga   2040
gaaacgcaag caccaattgt acaagtaaat ggtccatata ctggcatgat caatgaaaaa   2100
attcaattta atagtgatgg gtcaaaggat acggatggag aaatagtttc ttatctttgg   2160
gattttggtg atggcgcgac aagtgaagca gcaaatccta ctcatgtata cgaaaatgaa   2220
ggaacttaca aagtgacgtt aaccgtgaaa aataataagg gacaagaaag taaagggcaa   2280
acaactgcca ctgtacagaa aggaggacag acagggcaag aacatgcgat gattattcca   2340
tttaataaac cactaaaagg tagtttgata gaaaatgata caaatgtcta tcaatttgac   2400
```

attacatcgc cagaagaaat agatatttct gtcgtaaatg aaaatcaaat tggcatgaca 2460
tgggtgcttt atcatgaatc tgataaggaa aactatgtag cgtatggaca ggaagatgga 2520
cagacaataa aaggtaagta caatgcgaaa ccaggaaagt attatttata cgtttataag 2580
tttgatgatg aagatggaac atataccgtt caagtacaaa atagtacaaa aacggagata 2640
gaaccaaaca atcgtccaga agaagccact atgcttccat ttcatacacc actaagcggt 2700
agtttaatgg aggatgatca tacggatgta tacgaattca atgttacatc tcctaaagaa 2760
atagatatat ctgttttaaa tgaaaaccaa attggcatga catgggtgct ttatcatgaa 2820
tcagatagcc aaaattatgc gtcttttgga caggaagacg gaaacatgat aaacggtaaa 2880
ttgaatgcaa agcctggaaa gtattattta tatgtttata aatttgaaaa tgagaacgga 2940
acatataccg ttcatgtaca gtaa 2964

<210> SEQ ID NO 4
<211> LENGTH: 3219
<212> TYPE: DNA
<213> ORGANISM: Lysinibacillus fusiformis

<400> SEQUENCE: 4
atgaagaaaa aatttacatt caatcagttg ttaattgggg ttagtacaat ggccatttcg 60
ttaggtggat tacaggcgga agcatcggca gcagaaaaaa cgccgtataa tgtattacaa 120
atgaaaccca ttggcataga aatgtcgaaa gatgaaatgg tgcattcgac aatggctgaa 180
gaaacattat cctatgaaga acgtttagaa atgggagatt tttcacaacg tccagcacca 240
attatggaac agatggatac acagcaattg caggagcagt actcgatggc agagcttaat 300
aatatgagca atcgtgagct tatccatacg cttggcagta tccgttggta ccaaattaca 360
gacttattcc aattcaatga tgacacaaaa gctttttatc aaaatgaaga gcgcatgcaa 420
gtaatcatca atgaattagg gaatagagga aattcgttta cgaaggaaga ttcaaagggg 480
atcgaaacat ttgttgaggt attgcgttct gctttttatg tagcgtttta taataatgaa 540
ctaggctatt taaatgagag aagtttccaa gataagtgtt taccagcatt aaatgaaata 600
gccaaaaatc caaactttaa acttggtaca gatgagcaag ataaagttgt atctgcctat 660
ggaaaattaa taggtaatgc ttctagtgat gtggaaaccg ttcaacatgc tacgaacatt 720
ttaaaacaat ataatgaaaa tctttctacc tatgaaagtg agaattcaaa aggacaagct 780
atttacgata taatacacgg cattgattat gatttgcagt cttatttata tgacactcgt 840
aaagaggcca atacaacgat gtggtatggg aagattgata gcttcataga ggaagttaat 900
aacattgccc taatacataa tgtgacggat agcaatagtt ggttaattaa taatggcatt 960
tattatgcag ggcgtttagg gcagttccat agcaatccta ataagggttt agaagtcgtt 1020
acacaagcga tgcatatgta tccctattta agtgaagctt attttgtggc agtagagcaa 1080
attacgacaa attatggtgg acgtgactta aacggaaata cggttgattt acaaaaagta 1140
cgtgaagaag gaaaaaaaca gtatctaccg aaaacatata catttgatga tggatcaatt 1200
gtattcaaaa cgggagatca agtaacggaa gataaaattc aaagattata ctgggctgca 1260
aaagaggtaa aggcacaata tcatcgtgta atcgggaatg atcaagcact agagcctggt 1320
aatgctgacg atatcttaac cgttgtcatt tataactctc ccgatcagta ccgattaaac 1380
cgacaattgt acggatatga aacaaataat ggtggtattt atattgaaga gactggaaca 1440
ttctttacat atgaacgtac acctgagcaa agtatttata gcttagaaga gctgttccgt 1500
catgaatata cgcacttttt acaaggtaga tttgaggtgc ctggtctatt cgggacgggt 1560
gatatgtatc aaaatgagcg actaacatgg ttccaggaag ggaatgcaga attttttgca 1620
gggtcaacac gtacaaatga cgttgtgcct cgtaagagca ttattagtgg attgtcacag 1680
gatccatcac aacgctatac tgctgaacaa acaatgtttg ccacatatgg ttcctgggat 1740
ttttataatt attcatttgc attacagtct tatatgtata cgcatcaatt cgatatgttt 1800
gatagaattc aagatttaat ccgcgcgaac gatgtgaaaa attatgatgc ctatcgtgac 1860
actttaagta aagattcaca gctgaatatg gaataccaag catatatgca gcaattgatc 1920
gataaccaag aaacatacga agtaccacaa gtagcagagg attatttaat gccgcatgaa 1980
ccaaaagcgt taaacgaagt acagcaagaa attgtcgata ttgcacatgt gaaagatgca 2040
aatatgacga aacaccagtc tcaatttttt aatacgttta cactcgaggg aacatatgta 2100
ggtagtgcaa cacagggtga atctcaagat tggaaaacga tgagtaagca agtaaaccaa 2160
atgctggagc aactgtctca aaaagagtgg agcggctata aaacaatgac tgcgtacttt 2220
gtcaactatc gtgtaaatgc ggcaaaccag ttcgagtatg atgtagtctt ccatggcgtt 2280
tccactgatg acggagaaac gcaagcacca attgtacaag taaatggtcc atatactggc 2340
atgatcaatg aaaaaattca atttaatagt gatgggtcaa aggatacgga tggagaaata 2400
gtttcttatc tttgggattt tggtgatggc gcgacaagtg aagcagcaaa tcctactcat 2460
gtatacgaaa atgaaggaac ttacaaagtg acgttaaccg tgaaaaataa taagggacaa 2520
gaaagtaaag ggcaaacaac tgccactgta cagaaaggag gacagacagg gcaagaacat 2580
gcgatgatta ttccatttaa taaaccacta aaaggtagtt tgatagaaaa tgatacaaat 2640
gtctatcaat ttgacattac atcgccagaa gaaatagata tttctgtcgt aaatgaaaat 2700
caaattggca tgacatgggt gctttatcat gaatctgata aggaaaacta tgtagcgtat 2760
ggacaggaag atggacagac aataaaaggt aagtacaatg cgaaaccagg aaagtattat 2820
ttatacgttt ataagtttga tgatgaagat ggaacatata ccgttcaagt acaaaatagt 2880 acaaaaaacgg agatagaacc aaacaatcgt ccagaagaag ccactatgct tccatttcat 2940
acaccactaa gcggtagttt aatggaggat gatcatacgg atgtatacga attcaatgtt 3000
acatctccta aagaaataga tatatctgtt ttaaatgaaa accaaattgg catgacatgg 3060
gtgctttatc atgaatcaga tagccaaaat tatgcgtctt ttggacagga agacggaaac 3120
atgataaacg gtaaattgaa tgcaaagcct ggaaagtatt atttatatgt ttataaattt 3180
gaaaatgaga acggaacata taccgttcat gtacagtaa 3219

<210> SEQ ID NO 5
<211> LENGTH: 21
<212> TYPE: DNA
<213> ORGANISM: Artificial Sequence
<220> FEATURE:
<223> OTHER INFORMATION: Forward primer

<400> SEQUENCE: 5
ggaaacaatc taaatgtgtc t 21

<210> SEQ ID NO 6
<211> LENGTH: 21
<212> TYPE: DNA
<213> ORGANISM: Artificial Sequence
<220> FEATURE:
<223> OTHER INFORMATION: Reverse primer -continued

<400> SEQUENCE: 6

```
ccgcctttaa aggctctccg a                                          21
```

COLLAGENASE AGENT AND USE THEREOF

TECHNICAL FIELD

The present invention relates to an enzyme agent (collagenase agent) comprising collagenase as an active ingredient, and use thereof.

BACKGROUND ART

The global marker of collagen peptides known as functional peptides has been predicted to grow. Among such collagen peptides, the tripeptide Gly-X-Y that is a minimum unit of collagen (collagen tripeptide; hereinafter also abbreviated as "CTP") is highly absorbed into the body and also has various functionalities. Thus, the use of CTP is considered to be highly valuable.

In order to efficiently produce CTP, protease (collagenase) capable of specifically cleaving collagen or gelatin at the position of a Gly residue and decomposing it even to a tripeptide is useful. Examples of the known collagenase may include collagenase derived from *Clostridium* sp. or *Vibrio* sp., and *Bacillus cereus* collagenase (belonging to Microbial collagenase (EC.3.4.24.3)). The collagenase-producing bacteria have biosafety level 2 (BSL2), and thus, the safety thereof has been concerned. Accordingly, it is said that the use of the collagenase-producing bacteria is not suitable for the production of CTP that is utilized for food use, medical use, etc.

As collagenase usable for food use, collagenase derived from *Streptomyces* sp. has been known (Patent Document 1). However, whether this collagenase can be utilized in the production of CTP has not been known. In addition, the existing collagenases are generally problematic in terms of stability. As microorganism-derived collagenase having excellent stability and high specific activity, *Vibrio hollisae*-derived collagenase (*Vibrio* sp. 1706B strain-derived collagenase disclosed in Patent Document 2) has been known (Patent Document 2 and Patent Document 3). However, the heat stability of the *Vibrio hollisae*-derived collagenase is 30° C. or lower, and it is practically insufficient.

Moreover, it has been known that various collagenases having different properties are present. For example, it has been known that *Clostridium histolyticum*-derived collagenase has two different collagenase types (I and II), and that collagenase I has higher activity on collagen and gelatin and lower activity on a short-chain peptide, than collagenase II does (Patent Document 4). Furthermore, it has also been known that *Clostridium histolyticum*-derived collagenase has a low decomposition rate of cleaving CTP from a collagen-like sequence (Patent Document 5).

Collagenase suitable for producing CTP usable for food use from collagen is required to be produced from safe collagenase-producing bacteria, to have collagen-decomposing ability or gelatin-decomposing ability, and to have CTP-producing ability. Preferably, such collagenase is also required to have high stability. However, collagenase that satisfies the aforementioned conditions and has been put to practical use has not yet been known.

On the other hand, collagenase suitable for edible meat tenderization use is required to be produced from safe collagenase-producing bacteria, and to be specific to collagen (i.e. does not act on lean meats), and preferably, this collagenase is also required to have high stability.

PRIOR ART DOCUMENTS

Patent Documents

Patent Document 1: JP Patent Publication (Kokoku) No. 5-16832 B (1993)

Patent Document 2: JP Patent Publication (Kokai) No. 8-70853 A (1996)

Patent Document 3: JP Patent Publication (Kokai) No. 2010-263880 A

Patent Document 4: JP Patent Publication (Kohyo) No. 2001-510331 A

Patent Document 5: JP Patent Publication (Kokai) No. 2018-183106 A

SUMMARY OF INVENTION

Objects to be Solved by the Invention

Under the above-described background, it is an object of the present invention to provide: highly safe protease (collagenase) that is useful for food or medical use, such as production of CTP; the use thereof; etc.

Means for Solving the Objects

The present inventors have screened a wide variety of microorganism-derived enzymes directed towards obtaining collagenase having high CTP-producing ability and high safety. As a result, it was revealed that a specific strain of *Lysinibacillus fusiformis* produces collagenase that corresponds to the aforementioned purpose. This collagenase exhibited collagenase-decomposing ability, gelatin-decomposing ability, and CTP-producing ability, and further, this collagenase could be expected to specifically act on collagen or gelatin. Thus, this collagenase was industrially highly valuable. On the other hand, as a result of further studies, the present inventors have succeeded in identifying and obtaining a gene encoding this collagenase, and at the same time, have clarified the properties of the collagenase. Notably, this collagenase exhibited the preferred properties of a meat tenderizer comprising an alkaline pH adjuster such as sodium bicarbonate, such that the collagenase had relatively high heat stability and relatively stable activity even in the alkaline range.

[1] An enzyme agent comprising, as an active ingredient, collagenase having an amino acid sequence having an identity of 90% or more to the amino acid sequence as set forth in SEQ ID NO: 1.

[2] The enzyme agent according to the above [1], wherein the collagenase is derived from *Lysinibacillus fusiformis.*

[3] The enzyme agent according to the above [1] or [2], which is for use in production of a collagen tripeptide.

[4] The enzyme agent according to the above [1] or [2], which is for use in tenderization of edible meat.

[5] A method for producing a collagen tripeptide, which is characterized in that it comprises allowing the enzyme agent according to the above [3] to act on collagen or gelatin.

[6] A method for tenderizing edible meat, which is characterized in that it comprises allowing the enzyme agent according to the above [4] to act on edible meat.

[7] A collagenase having an amino acid sequence having an identity of 99% or more to the amino acid sequence as set forth in SEQ ID NO: 1.

[8] A gene encoding the collagenase according to the above [7].

[9] The gene according to the above [8] having the nucleotide sequence as set forth in SEQ ID NO: 3 or 4.

BRIEF DESCRIPTION OF DRAWINGS

FIG. 1 shows the amino acid sequence of collagenase derived from the *Lysinibacillus fusiformis* 57413 strain. The enclosure indicates a predicted signal sequence. The underline indicates a pro-sequence.

FIG. 2 shows the optimal temperature of collagenase derived from the *Lysinibacillus fusiformis* 57413 strain.

FIG. 3 shows the temperature stability of collagenase derived from the *Lysinibacillus fusiformis* 57413 strain.

FIG. 4 shows the optimal pH of collagenase derived from the *Lysinibacillus fusiformis* 57413 strain.

FIG. 5 shows the pH stability of collagenase derived from the *Lysinibacillus fusiformis* 57413 strain.

FIG. 6 shows the low-temperature reactivity of collagenase.

FIG. 7 shows the results obtained by confirming the ability of the present enzyme to generate Gly-Glu-Arg that is a collagen tripeptide.

FIG. 8 shows the results obtained by confirming the ability of the present enzyme to generate Gly-Pro-Hyp that is a collagen tripeptide.

FIG. 9 shows the results obtained by confirming the ability of the present enzyme to generate Gly-Pro-Ala that is a collagen tripeptide.

FIG. 10 shows the results obtained by measuring the effect of the present enzyme to tenderize pork ribs.

FIG. 11 shows the results obtained by measuring the effect of the present enzyme to tenderize beef chuck eye roll.

EMBODIMENT OF CARRYING OUT THE INVENTION

1. Collagenase Agent and Active Ingredient Thereof (Collagenase)

A first aspect of the present invention relates to an enzyme agent (collagenase agent). The enzyme agent of the present invention (hereinafter also referred to as "the present enzyme agent") comprises, as an active ingredient, collagenase (hereinafter also referred to as "the present enzyme"). The enzyme agent of the present invention is useful for production of a collagen tripeptide and tenderization of meat (the details will be described later). The collagenase serving as an active ingredient, namely, the present enzyme consists of the amino acid sequence as set forth in SEQ ID NO: 1, or an amino acid sequence equivalent to the amino acid sequence as set forth in SEQ ID NO: 1. Herein, the term "equivalent amino acid sequence" means an amino acid sequence that is partially different from the reference amino acid sequence (i.e. the amino acid sequence as set forth in SEQ ID NO: 1) but such difference does not substantially influence on the function of the protein (which is herein collagen-decomposing ability). Accordingly, an enzyme having such an equivalent amino acid sequence catalyzes a collagen-decomposing reaction. The degree of the activity is not particularly limited, as long as the function of collagenase can be exhibited. However, the activity of the enzyme having such an equivalent amino acid sequence is preferably equivalent to or higher than the activity of an enzyme having the reference amino acid sequence (i.e. an enzyme having the amino acid sequence as set forth in SEQ ID NO: 1).

The amino acid sequence as set forth in SEQ ID NO: 1 is the amino acid sequence of collagenase derived from *Lysinibacillus fusiformis* (mature body). Besides, the amino acid sequence of collagenase derived from *Lysinibacillus fusiformis*, which also has a signal peptide and a pro-sequence, is shown in SEQ ID NO: 2.

A "partial difference in an amino acid sequence" is generated, for example, as a result of a deletion or a substitution of one or more amino acids in the amino acids constituting the amino acid sequence, or an addition or an insertion of one or more amino acids into the amino acid sequence, or any given combination thereof. Such a partial difference in the amino acid sequence is acceptable, as long as the collagen-decomposing activity is retained (the activity may be slightly fluctuated). As far as this condition is satisfies, the position of the amino acid sequence, in which the difference is found, is not particularly limited. In addition, such difference may be generated in multiple sites (places) on the amino acid sequence.

The number of amino acids providing such a partial difference in the amino acid sequence is a number corresponding to, for example, less than about 10%, preferably less than about 8%, more preferably about 6%, even more preferably less than about 4%, further preferably less than about 2%, and most preferably less than about 1%, with respect to the entire amino acids that constitute the amino acid sequence. Accordingly, the equivalent protein has an identity of, for example, about 90% or more, preferably about 92% or more, more preferably about 94% or more, even more preferably about 96% or more, further preferably about 98% or more, and most preferably about 99% or more, to the reference amino acid sequence.

A typical example of a "partial difference in the amino acid sequence" is that a mutation (a change) is generated in the amino acid sequence, as a result of a deletion or a substitution of 1 to 40 (preferably 1 to 30, more preferably 1 to 10, even more preferably 1 to 7, further preferably 1 to 5, and still further preferably 1 to 3) amino acids in the amino acids constituting the amino acid sequence, or an addition or an insertion of 1 to 40 (preferably 1 to 30, more preferably 1 to 10, even more preferably 1 to 7, further preferably 1 to 5, and still further preferably 1 to 3) amino acids into an amino acid sequence, or any given combination thereof.

Preferably, an equivalent amino acid sequence is obtained by the occurrence of conservative amino acid substitution in amino acid residues that are not essential for collagen-decomposing ability. The term "conservative amino acid substitution" is used herein to mean that a certain amino acid residue is substituted with an amino acid residue having a side chain with similar properties. Amino acid residues are classified into several families, depending on the side chain thereof; namely, basic side chains (for example, lysine, arginine, and histidine), acidic side chains (for example, aspartic acid and glutamic acid), uncharged polar side chains (for example, glycine, asparagine, glutamine, serine, threonine, tyrosine, and cysteine), non-polar side chains (for example, alanine, valine, leucine, isoleucine, proline, phenylalanine, methionine, and tryptophan), β-branched side chains (for example, threonine, valine, and isoleucine), aromatic side chains (for example, tyrosine, phenylalanine, tryptophan, and histidine), etc. The conservative amino acid substitution is preferably a substitution occurring between amino acid residues in an identical family.

By the way, identity (%) of two amino acid sequences can be determined, for example, by the following procedures. First, two sequences are aligned such that an optimal comparison can be made (for example, a gap may be introduced into a first sequence, so that the alignment with a second sequence may be optimized). When a molecule (amino acid residue) in a specific position of the first sequence is identical to a molecule in a corresponding position in the second sequence, it can be said that the molecules at the positions are identical to each other. The identity of the two sequences is a function of the number of identical positions common in the two sequences (i.e. identity (%)=the number of identical positions/total number of positions×100), and preferably, the number and size of gaps used for optimization of the alignment are also taken into consideration.

Comparison of two sequences and determination of identity can be realized using mathematical algorithms. A specific example of the mathematical algorithm that can be utilized in comparison of sequences may be an algorithm that is described in Karlin and Altschul (1990) Proc. Natl. Acad. Sci. USA 87: 2264-68 and is modified in Karlin and Altschul (1993) Proc. Natl. Acad. Sci. USA 90: 5873-77, but the example of the mathematical algorithm is not limited thereto. Such algorithm is incorporated into NBLAST program and XBLAST program (version 2.0) described in Altschul et al. (1990) J. Mol. Biol. 215: 403-10. In order to obtain an amino acid sequence equivalent to a reference amino acid sequence, for example, a BLAST polypeptide search may be carried out using XBLAST program with score=50 and word length=3. In order to obtain a gap alignment for comparison, Gapped BLAST described in Altschul et al. (1997) Amino Acids Research 25 (17): 3389-3402 can be utilized. When BLAST and Gapped BLAST are utilized, the default parameters of the corresponding programs (for example, XBLAST and NBLAST) can be used. Please refer to http://www.ncbi.nlm.nih.gov for details. Another example of the mathematical algorithm that can be utilized for sequence comparison may be the algorithm described in Myers and Miller (1988) Comput Appl Biosci. 4: 11-17. Such algorithm is incorporated into the ALIGN program available on, for example, the GENESTREAM network server (IGH Montpellier, France) or the ISREC server. When the ALIGN program is utilized for comparison of amino acid sequences, for example, a PAM120 residue mass table can be used with a gap length penalty=12 and a gap penalty=4.

The identity of two amino acid sequences can be determined, employing the GAP program in the GCG software package, using a Blossom 62 matrix or PAM250 matrix, with gap weight=12, 10, 8, 6, or 4, and gap length weight=2, 3 or 4.

The collagenase that is an active ingredient of the present enzyme agent, namely, the present enzyme may be a part of a larger protein (for example, a fusion protein). Examples of a sequence to be added to such a fusion protein may include sequences that are useful for purification, such as multiple histidine residues, and additional sequences that ensure stability during recombinant production.

The present enzyme can be obtained by culturing microorganisms that generate the present collagenase (i.e. a collagenase-generating strain), for example, *Lysinibacillus fusiformis*. The collagenase-generating strain may be either a wild-type strain or a mutant strain (such a mutant strain is obtained, for example, by ultraviolet irradiation). A specific example of the collagenase-generating strain may be *Lysinibacillus fusiformis* IFO 3528 (NBRC 15717). The *Lysinibacillus fusiformis* IFO 3528 (NBRC15717) is a strain conserved at NBRC (National Institute of Technology and Evaluation, Biological Resource Center), and this strain can be furnished by going through prescribed procedures.

The present enzyme can be prepared using a culture solution and/or a cell mass of microorganisms that generate the present enzyme. The culture conditions or the culture methods are not particularly limited, as long as the present enzyme can be produced thereby. That is to say, the methods or the culture conditions that are adapted to the culture of the used microorganisms can be determined, as appropriate, under conditions in which the present enzyme is produced. Regarding the culture method, either liquid culture or solid culture may be applied, and liquid culture is preferably utilized. Taking the liquid culture as an example, the culture conditions will be described below.

The medium is not particularly limited, as long as it is a medium in which the used microorganisms can grow. Examples of the medium that can be used herein may include those to which the following substances are added: carbon sources, such as glucose, sucrose, gentiobiose, soluble starch, glycerin, dextrin, molasses, and organic acids; nitrogen sources, such as ammonium sulfate, ammonium carbonate, ammonium phosphate, ammonium acetate, or gelatin, peptone, yeast extract, corn steep liquor, casein hydrolysate, bran, and meat extract; and further, inorganic salts, such as potassium salts, magnesium salts, sodium salts, phosphates, manganese salts, iron salts and zinc salts. In order to promote the growth of the used microorganisms, vitamins, amino acids and the like may be added to the medium. The pH of the medium is adjusted to, for example, about 3 to 8, preferably about 4 to 7. The culture temperature is usually about 20° C. to 40° C., preferably about 25° C. to 35° C., and the microorganisms are cultured for 1 to 20 days, and preferably 3 to 10 days, under aerobic conditions. As a culture method applied herein, for example, a shaking culture method, or an aerobic deep culture method using a jar fermenter, can be utilized.

After completion of the culture performed under the above-described conditions, the enzyme of interest is recovered from the culture solution or the culture mass. When the enzyme is recovered from the culture solution, for example, the culture supernatant is filtered, centrifuged, etc. to remove insoluble matters, and thereafter, the resultant is separated and purified by appropriately combining concentration using an ultrafiltration membrane, salting-out such as ammonium sulfate precipitation, dialysis, and various types of chromatography using ion exchange resin, etc., thereby obtaining the present enzyme. On the other hand, when the enzyme is recovered from the cell mass, for example, the cell mass is crushed by a pressure treatment, an ultrasonic treatment, etc., and is then separated and purified in the same manner as that described above, so as to obtain the present enzyme. Besides, the cell mass may be previously recovered from the culture solution by filtration, a centrifugation treatment, etc., and thereafter, the above-described series of steps (crushing, separation, and purification of the cell mass) may be carried out.

Also, the present enzyme can be easily prepared by a genetic engineering technique. For example, the present enzyme can be prepared by transforming suitable host cells (for example, *Escherichia coli*) with DNA encoding the present enzyme, and then recovering the protein expressed in the transformant. The recovered protein is appropriately purified, depending on the purpose. As such, if the enzyme of interest is obtained as a recombinant protein, various modifications can be carried out thereon. For example, a DNA encoding the present enzyme and another appropriate DNA are inserted into an identical vector, and a recombinant protein is produced using the vector, so that the present enzyme consisting of a recombinant protein, in which any given peptides or proteins are ligated to each other, can be obtained. In addition, modification may be carried out, so that addition of a sugar chain and/or a lipid or the processing of the N-terminus or the C-terminus may occur. By performing the aforementioned modification, simplification of the extraction and purification of a recombinant protein, addition of biological functions, etc. can be carried out.

Generally, the expression of a gene and the recovery of a gene expression product (the present enzyme) are carried out, utilizing an appropriate host-vector system, as described above. However, a cell-free synthesis system may also be utilized. Herein, the term "cell-free synthesis system (a cell-free transcription system or a cell-free transcription/translation system)" means that, not using living cells, but using a ribosome, a transcription/translation factor or the like derived from living cells (or obtained by a genetic engineering technique), from a nucleic acid (DNA or mRNA) used as a template, mRNA or a protein encoded by the nucleic acid is synthesized in vitro. In general, in the cell-free synthesis system, a cell extract obtained by purifying, as necessary, a cell-disintegrated solution is used. The cell extract generally comprises a ribosome, various types of factors such as an initiation factor, and various types of enzymes such as tRNA, which are necessary for protein synthesis. When a protein is synthesized, various types of amino acids, energy sources such as ATP or GTP, and other substances necessary for protein synthesis, such as creatine phosphate, are added to the aforementioned cell extract. As a matter of course, upon the synthesis of a protein, a ribosome, various types of factors, and/or various types of enzymes, and the like, which are prepared separately, may also be added to the aforementioned cell extract, as necessary.

The development of a transcription/translation system, in which various molecules (factors) necessary for protein synthesis have been reconstructed, has also been reported (Shimizu, Y. et al.: Nature Biotech., 19, 751-755, 2001). In this synthesis system, genes of 31 types of factors composed of: 3 types of initiation factors, 3 types of elongation factors, 4 types of factors associated with termination, 20 types of aminoacyl tRNA synthesis enzymes that allow each amino acid to bind to tRNA, and a methionyl tRNA formyl transfer enzyme, which constitute a protein synthesis system of bacteria, are amplified from an *Escherichia coli* genome, and then, using these amplified products, a protein synthesis system is reconstructed in vitro. In the present invention, such a reconstructed synthesis system may be utilized.

The term "cell-free transcription/translation system" is exchangeably used with the term "cell-free protein synthesis system," "in vitro translation system" or "in vitro transcription/translation system." In the in vitro translation system, RNA is used as a template to synthesize a protein. As such template RNA, total RNA, mRNA, an in vitro transcriptional product or the like is used. On the other hand, in the in vitro transcription/translation system, DNA is used as a template. The template DNA should comprise a ribosome-binding region, and preferably comprises an appropriate terminator sequence. In addition, in the in vitro transcription/translation system, in order to promote continuous progression of the transcription reaction and the translation reaction, conditions, in which factors necessary for each reaction are added, are established.

The purified enzyme obtained as described above is pulverized, for example, by freeze drying, vacuum drying, or spray drying, so that the enzyme can be provided in the form of powders. At that time, the purified enzyme may be previously dissolved in an acetate buffer, a phosphate buffer, a triethanolamine buffer, a Tris-HCl buffer, or a GOOD buffer. Preferably, an acetate buffer, a phosphate buffer, or a triethanolamine buffer can be used. Besides, examples of the GOOD buffer used herein may include PIPES, MES, and MOPS.

The purification degree of the enzyme is not particularly limited, and for example, the enzyme can be purified, so that the Pz-peptide-decomposing activity becomes 2 to 20 (U/g). In addition, the final form of the enzyme may be either a liquid or a solid (including powders).

As a result of the studies conducted by the present inventors, the properties of collagenase derived from *Lysinibacillus fusiformis*, having an amino acid sequence as set forth in SEQ ID NO: 1, have been determined as follows (please refer to the after-mentioned Examples for details). Accordingly, the present enzyme can also be specified by the following enzymatic properties. It is to be noted that the details of the measuring conditions, measuring procedures, etc. of collagenase activity necessary for evaluation of each enzymatic property will be described in the after-mentioned Examples.

(1) Action

The present enzyme is collagenase, which acts on collagen or gelatin to generate a collagen tripeptide.

(2) Optimal Temperature

The optimal temperature of the present enzyme is 40° C.

(3) Temperature Stability

Even if the present enzyme is treated in a Tris-HCl buffer under conditions of pH 7 and a temperature of 40° C. or lower (0° C. to 40° C.) for 30 minutes, the activity of the enzyme is not substantially decreased.

(4) Optimal pH

The optimal pH of the present enzyme is about 7. The optimal pH is determined, for example, based on the results measured in an acetate buffer in a pH range from pH 4 to 6, in a PIPES buffer in a pH range from pH 6 to 7, or in a Tris-HCl buffer (Tris-HCl) in a pH range from pH 7 to 9.

(5) pH Stability

The present enzyme exhibits stable activity in a pH range from pH 5 to 9.5. For example, if the pH of an enzyme solution to be treated is within this range, the present enzyme exhibits an activity of 85% or more of the maximum activity, after it has been treated at 30° C. for 30 minutes. The pH stability is determined, for example, based on the results measured in an acetate buffer in a pH range from pH 4 to 6, in a PIPES buffer in a pH range from pH 6 to 7, in a Tris-HCl buffer (Tris-HCl) in a pH range from pH 7 to 9, or in a glycine buffer in a pH range from pH 9 to 11.

(6) Low-Temperature Reactivity

When the enzyme activity of the present enzyme at a reaction temperature of 40° C. is defined as 100%, the relative activity of the present enzyme at a reaction temperature of 30° C. is 40% or more, and the relative activity of the present enzyme at a reaction temperature of 20° C. is 10% or more.

By allowing the present enzyme to act on collagen or gelatin, there can be obtained the collagen tripeptides Gly- X-Y (CTPs), namely, Gly-Glu-Arg, Gly-Pro-Hyp, Gly-Pro-Ala, Gly-Ala-Hyp, etc. (wherein Pro: proline, Hyp: hydroxyproline, and Ala: alanine), which have Gly (glycine) at the N-terminus. The present enzyme is characterized in that it provides a high yield of Gly-Glu-Arg that is a functional peptide, when the present enzyme is allowed to act on collagen or gelatin.

The content of the active ingredient (the present enzyme) in the present enzyme agent is not particularly limited. For example, the content of the active ingredient can be determined or adjusted, so that the Pz-peptide-decomposing activity per gram of the present enzyme agent becomes 1 U to 500 U, and preferably 10 U to 300 U. The enzyme agent of the present invention is usually provided in the form of a solid (for example, an immobilized enzyme formed by immobilizing the present enzyme on a material capable of immobilizing the enzyme on the surface or inside thereof, such as a granule, a powder, a silica, or a porous polymer) or a liquid. The present enzyme agent may comprise an excipient, a buffer agent, a suspending agent, a stabilizer, a preservative, an antiseptic, a normal saline, etc., as well as the active ingredient (the present enzyme). As such an excipient, lactose, sorbitol, D-mannitol, maltodextrin, saccharose, etc. can be used. As such a buffer agent, phosphate, citrate, acetate, etc. can be used. As such a stabilizer, propylene glycol, ascorbic acid, etc. can be used. As such a preservative, phenol, benzalkonium chloride, benzyl alcohol, chlorobutanol, methylparaben, etc. can be used. As such an antiseptic, benzalkonium chloride, paraoxybenzoic acid, chlorobutanol, etc. can be used.

2. Gene

According to a second aspect of the present invention, a nucleic acid associated with the present enzyme is provided. That is to say, provided are: a gene encoding the present enzyme; a nucleic acid that can be used as a probe for identifying a nucleic acid encoding the present enzyme; and a nucleic acid that can be used as a primer for amplification, mutation, etc. of a nucleic acid encoding the present enzyme. In one embodiment, the gene of the present invention consists of DNA encoding the amino acid sequence as set forth in SEQ ID NO: 1. Specific examples of the present embodiment may include DNA having the nucleotide sequence as set forth in SEQ ID NO: 3 and DNA having the nucleotide sequence as set forth in SEQ ID NO: 4. The former DNA (SEQ ID NO: 3) encodes only the amino acid sequence of a mature body (SEQ ID NO: 1), whereas the latter DNA (SEQ ID NO: 4) encodes a signal peptide and a pro-sequence, in addition to the mature body (the amino acid sequence as set forth in SEQ ID NO: 1).

The gene encoding the present enzyme is typically utilized in preparation of the present enzyme. According to a genetic engineering preparation method using the gene encoding the present enzyme, it is possible to obtain the present enzyme in a more homogeneous state. In addition, it is said that this method is a method preferably used in the case of preparing a large amount of the present enzyme. Besides, the use of the gene encoding the present enzyme is not limited to the preparation of the present enzyme. For example, the present nucleic acid can also be used as an experimental tool for elucidating the action mechanism of the present enzyme, or as a tool for designing or preparing a mutant (a modified body) of the present enzyme.

In the present description, the phrase "the gene encoding the present enzyme" means a nucleic acid for providing the present enzyme, when the nucleic acid is allowed to express. Thus, the gene encoding the present enzyme includes not only a nucleic acid having a nucleotide sequence corresponding to the amino acid sequence of the present enzyme, but also a nucleic acid formed by adding a sequence that does not encode the amino acid sequence to the aforementioned nucleic acid. Moreover, codon degeneracy is also taken into consideration.

With reference to the present description or the sequence information disclosed in the sequence listing attached herewith, the nucleic acid of the present invention can be prepared in an isolated state according to a standard genetic engineering technique, a molecular biological technique, a biochemical technique, chemical synthesis, a PCR method (for example, overlap PCR), or a combination thereof.

According to another embodiment of the present invention, provided is a nucleic acid, in which when the nucleic acid is compared with the nucleotide sequence of the gene encoding the present enzyme, the function of a protein encoded thereby is equivalent, but the nucleotide sequence thereof is partially different from the nucleotide sequence of the gene encoding the present enzyme (which is hereinafter also referred to as an "equivalent nucleic acid", and the nucleotide sequence of the equivalent nucleic acid is also referred to as an "equivalent nucleotide sequence"). An example of such an equivalent nucleic acid may be DNA that encodes a protein having a nucleotide sequence comprising a substitution, deletion, insertion, addition or inversion of one or more nucleotides, based on the nucleotide sequence of the nucleic acid encoding the enzyme of the present invention, and having enzyme activity characteristic of the present enzyme (i.e. collagenase activity). Substitution, deletion, etc. of a nucleotide(s) may occur in multiple sites. The term "multiple" is used herein to mean for example, 2 to 40 nucleotides, preferably 2 to 20 nucleotides, and more preferably 2 to 10 nucleotides, although the number of nucleotides is different depending on the positions or types of amino acid residues in the three-dimensional structure of a protein encoded by the nucleic acid. The equivalent nucleic acid has an identity of, for example, 90% or more, preferably 92% or more, more preferably 94% or more, even more preferably 96% or more, further preferably about 98% or more, and most preferably 99% or more, with respect to the nucleotide sequence serving as a reference (SEQ ID NO: 3 or SEQ ID NO: 4).

Such an equivalent nucleic acid as described above can be obtained by, for example, a restriction enzyme treatment, a treatment with exonuclease, DNA ligase, etc., introduction of a mutation according to a site-directed mutagenesis (Molecular Cloning, Third Edition, Chapter 13, Cold Spring Harbor Laboratory Press, New York) or a random mutation introduction method (Molecular Cloning, Third Edition, Chapter 13, Cold Spring Harbor Laboratory Press, New York), etc. The equivalent nucleic acid can also be obtained by other methods such as ultraviolet irradiation.

Another embodiment of the present invention relates to a nucleic acid having a nucleotide sequence complementary to the nucleotide sequence of the gene of the present invention that encodes the present enzyme. A further embodiment of the present invention provides a nucleic acid having a nucleotide sequence that is, at least, about 90%, 92%, 94%, 96%, 98% or 99% identical to the nucleotide sequence of the gene of the present invention that encodes the present enzyme, or to a nucleotide sequence complementary to the nucleotide sequence of the gene of the present invention that encodes the present enzyme.

A still further embodiment of the present invention relates to a nucleic acid having a nucleotide sequence that hybridizes under stringent conditions to a nucleotide sequence complementary to the nucleotide sequence of the gene of the present invention that encodes the present enzyme or a nucleotide sequence equivalent thereto. The term "stringent conditions" is used herein to mean conditions under which, what is called, a specific hybrid is formed, but a non-specific hybrid is not formed. Such stringent conditions are known to those skilled in the art, and can be determined, for example, with reference to Molecular Cloning (Third Edition, Cold Spring Harbor Laboratory Press, New York) or Current protocols in molecular biology (edited by Frederick M. Ausubel et al., 1987). The stringent conditions may be, for example, conditions in which incubation is performed at about 50° C., using a hybridization solution (50% formamide, 10×SSC (0.15 M NaCl, 15 mM sodium citrate, pH 7.0), 5×Denhardt solution, 1% SDS, 10% dextran sulfate, 10 µg/ml denatured salmon sperm DNA, and 50 mM phosphate buffer (pH 7.5)), and thereafter, washing is performed at about 65° C., using 0.1×SSC and 0.1% SDS. More preferred stringent conditions may be, for example, conditions of using, as a hybridization solution, 50% formamide and 5×SSC (0.15 M NaCl, 15 mM sodium citrate, pH 7.0), 1×Denhardt solution, 1% SDS, 10% dextran sulfate, 10 µg/ml denatured salmon sperm DNA, 50 mM phosphate buffer (pH 7.5)).

A still further embodiment of the present invention provides a nucleic acid having a part of the nucleotide sequence of the gene of the present invention that encodes the present enzyme or a nucleotide sequence complementary thereto (a nucleic acid fragment). Such a nucleic acid fragment can be used to, for example, detect, identify, and/or amplify a nucleic acid having the nucleotide sequence of the gene of the present invention that encodes the present enzyme, etc. For example, the nucleic acid fragment is designed to, at least, comprise a portion that hybridizes to a continuous nucleotide portion (for example, a length of about 10 to about 100 nucleotides, preferably about 20 to about 100 nucleotides, and more preferably about 30 to about 100 nucleotides) in the nucleotide sequence of the gene of the present invention that encodes the present enzyme. When the nucleic acid fragment is utilized as a probe, it can be labeled. For labeling, for example, a fluorescent substance, an enzyme, or a radioisotope can be used.

A further aspect of the present invention relates to recombinant DNA comprising the gene of the present invention (i.e. a gene encoding the present enzyme). The recombinant DNA of the present invention is provided in the form of, for example, a vector. The term "vector" is used in the present description to mean a nucleic acid molecule capable of transporting a nucleic acid inserted in the nucleic acid molecule into a target such as a cell.

Depending on intended purpose (cloning or the expression of a protein), or taking into consideration of the type of a host cell, a suitable vector is selected. Examples of the vector having *Escherichia coli* as a host may include M13 phage or a modified body thereof, λ phage or a modified body thereof, and pBR322 or a modified body thereof (pB325, pAT153, pUC8, etc.). Examples of the vector having yeast as a host may include pYepSec1, pMFa, and pYES2. Examples of the vector having an insect cell as a host may include pAc and pVL. Examples of the vector having a mammalian cell as a host may include pCDM8 and pMT2PC.

The vector of the present invention is preferably an expression vector. The term "expression vector" means a vector that is capable of introducing a nucleic acid inserted in the vector into a cell of interest (a host cell) and that is also capable of allowing the nucleic acid to express in the host cell. The expression vector usually comprises a promoter sequence necessary for the expression of the inserted nucleic acid, an enhancer sequence for promoting the expression, and the like. An expression vector comprising a selective marker can also be used. In the case of using such an expression vector, the presence or absence of the introduction of the expression vector (and the degree thereof) can be confirmed by utilizing the selective marker.

Insertion of the nucleic acid of the present invention into the vector, insertion of a selective marker (if necessary), insertion of a promoter (if necessary), and the like can be carried out by using a standard recombinant DNA technique (for example, a publicly known method using restriction enzyme and DNA ligase, which can refer to Molecular Cloning, Third Edition, 1.84, Cold Spring Harbor Laboratory Press, New York).

In terms of the ease of handling, microorganisms such as *Escherichia coli, Bacillus subtilis*, and budding yeast (*Saccharomyces cerevisiae*) are preferably used as host cells. However, any host cells can be utilized, as long as they are capable of replicating recombinant DNA and expressing the gene of the present enzyme. In the case of utilizing a T7 promoter, the used *Escherichia coli* may be, for example, the *Escherichia coli* BL21(DE3)pLysS. In the case of not using a T7 promoter, the used *Escherichia coli* may be, for example, the *Escherichia coli* JM109. In addition, examples of the budding yeast may include the budding yeast SHY2, the budding yeast AH22, and the budding yeast INVSc1 (Invitrogen).

Another aspect of the present invention relates to a microorganism (i.e. a transformant) comprising the recombinant DNA of the present invention. The microorganism of the present invention can be obtained by transfection or transformation using the above-described vector of the present invention. Such transfection or transformation can be carried out, for example, by a calcium chloride method (Journal of Molecular Biology (J. Mol. Biol.), Vol. 53, p. 159 (1970)), a Hanahan method (J. Mol. Biol., Vol. 166, p. 557 (1983)), an SEM method (Gene, Vol. 96, p. 23 (1990)), a method of Chung, et al. (Proceedings of the National Academy of Sciences of the USA. Vol. 86, p. 2172 (1989)), a calcium phosphate coprecipitation method, electroporation (Potter, H. et al., Proc. Natl. Acad. Sci. U.S.A. 81, 7161-7165 (1984)), and lipofectin (Felgner, P. L. et al., Proc. Natl. Acad. Sci. U.S.A. 84, 7413-7417 (1984)). Besides, the microorganism of the present invention can be utilized to produce the enzyme of the present invention.

3. Use of the Present Enzyme Agent

A further aspect of the present invention relates to the uses of the present enzyme agent. As a first use, provided is a method for producing a collagen tripeptide (CTP) (hereinafter referred to as a "CTP production method"). According to the CTP production method of the present invention, the present enzyme agent is allowed to act on collagen or gelatin (denatured collagen). For example, the present enzyme agent is added to a solution of collagen or gelatin, and a reaction is then carried out under conditions of, for example, 20° C. to 50° C., and preferably 30° C. to 40° C., for a predetermined period of time (for example, 1 hour to 12 hours). As a result of a decomposition reaction by collagenase as an active ingredient of the present enzyme agent, a collagen tripeptide is generated. The composition, ratio, etc. of CTP in the product can be fluctuated depending on the type, origin, etc. of the used substrate (collagen or gelatin).

According to the production method of the present invention, a composition containing a tripeptide having Gly at the N-terminus thereof (for example, Gly-Glu-Arg, Gly-Pro-Hyp, Gly-Pro-Ala, or Gly-Ala-Hyp), namely, a CTP-containing composition can be obtained. CTP can be generated by the single use of the present enzyme agent, and this is one of the characteristics of the present invention. However, it is also possible to use the present enzyme agent in combination with another collagenase or protease, or with peptidase, so as to achieve the improvement of production efficiency, etc.

The origin of the used collagen/gelatin is not particularly limited, and examples of the origin of the used collagen/gelatin may include fish, a pig, a bovine, and a chicken. Commercially available collagen or gelatin may also be used. The method of preparing such collagen or gelatin is not particularly limited, either. For example, a raw material (the skin, bone, tendon, fish scales, etc. of animals) is washed with water and is then dried, and thereafter, the resultant is subjected to a decalcification treatment using hydrochloric acid or the like, as necessary. After washing, the resultant is treated with caustic soda, hydrochloric acid, etc. to obtain crude collagen. In addition, the crude collagen is subjected to a thermal treatment, so that gelatin can be extracted.

After completion of an enzymatic reaction using the present enzyme agent, a purification treatment (for example, filtration, ion exchange, or activated carbon treatment) is carried out, as necessary, for the removal of insoluble components, the improvement of purity, discoloration, deodorization, etc.

A second use of the present enzyme agent is the quality improvement of edible meats. More specifically, for tenderization of edible meats, the enzyme agent of the present invention is utilized. That is, a method for tenderizing meats is provided. By using the enzyme agent of the present invention, collagen contained in edible meats can be specifically cleaved, and thereby, edible meats with improved texture (typically, edible meats having soft texture can be obtained, while suppressing dryness. The edible meats, with which the enzyme is allowed to react, are not particularly limited. Edible meats containing abundant collagen (for example, shank and tendon) are preferred targets to be treated. As described in Examples later, it has been confirmed that the present enzyme agent has an action not to tenderize lean meats in pork ribs but to tenderize fatty meats containing a large amount of collagen, and further that the present enzyme agent also has an action to tenderize tendons in beef chuck eye roll. The term "edible meat" is used herein to include edible meat-processed products. Accordingly, the method for tenderizing meats of the present invention can also be applied to the improvement of the texture of restructured meats, hams and sausages, etc. According to the method for tenderizing meats of the present invention, the present enzyme agent is allowed to act on edible meats. The present enzyme agent may be allowed to act on edible meats according to a method of immersing edible meats in an enzyme solution (a solution containing the enzyme agent), a method of infiltrating an enzyme solution into edible meats by a pressure treatment, a method of injecting an enzyme solution into edible meats, a method of injecting an enzyme solution into edible meats and then tumbling the meats (a treatment of mechanically infiltrating an enzyme solution into edible meats), or other methods. The temperature conditions applied when the enzyme agent is allowed to act on edible meats are, for example, 4° C. to 40° C., preferably 4° C. to 30° C., more preferably 4° C. to 25° C., and further preferably 4° C. to 20° C. The time required for allowing the enzyme agent to act on edible meats (i.e. the reaction time) is, for example, 1 hour to 1 day.

EXAMPLES

1. Screening for Collagenase-Generating Strain

In order to find out collagenase that can be utilized for food products, a first screening was carried out using collagenase activity as an indicator from the library of Amano Enzyme Inc., and 113 types of production strains with biosafety level 1 (BSL1), which exhibited high activity, were selected.

Subsequently, as a second screening, the culture supernatant of each of the selected 113 types of production strains was allowed to react with gelatin, and the content rate of peptides having Gly at the N-terminus thereof in the reaction product was then evaluated. As a result, 19 types of production strains were selected. The total peptide amount was quantified using a ninhydrin reagent. On the other hand, the amount of the peptides having Gly at the N-terminus thereof was quantified using Collagen Quantification Kit (manufactured by COSMO BIO COMPANY, LIMITED).

As a third screening, tripeptides were partially purified from the reaction products of the culture supernatants of the 19 types of production strains with gelatin according to gel filtration chromatography, and were then analyzed according to reverse phase chromatography. The culture supernatants of the production strains that seemed to be promising from the analysis results were partially purified, and thereafter, the CTP-producing ability of collagenase was evaluated, so that the *Lysinibacillus fusiformis* 57413 strain was finally selected as a collagenase-producing bacterium.

2. Preparation and Purification of Collagenase Crude Enzyme Solution of 57413 Strain The 57413 strain was subjected to an aerated and agitated culture in a gelatin-containing medium (5% fish gelatin, 0.5% yeast extract, and 2% NaCl) at 30° C. for 2 days. Thereafter, the obtained culture solution was centrifuged, and the supernatant was then filtrated using diatomaceous earth to obtain a crude enzyme solution. Thereafter, the enzyme was purified using hydrophobic chromatography (Pheny HP, manufactured by GE Healthcare Life Sciences) and anion exchange chromatography (DEAE FF, manufactured by GE Healthcare Life Sciences).

3. Confirmation of Gene Sequence of Collagenase from 57413 Strain

The 57413 strain was cultured in an SCD liquid medium overnight at 30° C., and the cell mass was then recovered by centrifugation. The recovered cell mass was suspended in a TE buffer, and DNA was then extracted using NucleoSpin (registered trademark) Microbial DNA (manufactured by Takara Bio, Inc.). Using the extracted DNA as a template, PCR was carried out employing the following upstream and downstream primers and PrimeSTAR (registered trademark) Max DNA Polymerase (manufactured by Takara Bio, Inc.). The amplified PCR product was subjected to a nucleotide sequence analysis using primers having homology with the inside and outside of the structural gene, so that the sequence of the PCR product was confirmed (FIG. 1).

```
Upstream:
forward primer:
                                        (SEQ ID NO: 5)
GGAAACAATCTAAATGTGTCT

Downstream:
reverse primer:
                                        (SEQ ID NO: 6)
CCGCCTTTAAAGGCTCTCCGA
```

4. Recombinant Expression of Collagenase

The 57413 strain collagenase gene (SEQ ID NO: 2) was introduced into pColdIII (manufactured by Takara Bio, Inc.) to construct an expression plasmid. Using the constructed expression plasmid, the *Escherichia coli* BL21 was transformed according to an ordinary method. The obtained transformant was cultured in an LB medium (supplemented with ampicillin) overnight at 37° C., and the obtained culture solution was then inoculated in a volume of 1% into an LB medium (supplemented with ampicillin) The obtained mixture was cultured at 37° C. for 2 hours, followed by addition of IPTG, and the thus obtained mixture was then cultured at 15° C. overnight. Thereafter, a cell mass was recovered from the obtained culture solution by centrifugation, and the cell mass was then disintegrated using an ultrasonic integrator. The supernatant was recovered by centrifugation, and was defined as a recombinant crude enzyme solution. The enzyme activity of this crude enzyme solution was confirmed by the following measurement methods. As a result, it was found that the crude enzyme solution had collagen-decomposing activity, pz-peptide-decomposing activity, and CTP-producing ability. Moreover, it was highly likely that the crude enzyme solution would not have casein-decomposing activity and would specifically act on collagen or gelatin.

Pz-Peptide-Decomposing Activity

The enzyme solution (100 μL) was added to 900 μL of 200 mM Tris-HCl buffer containing 1 mg/mL Pz-peptide (Pz-Pro-Leu-Gly-Pro-D-Arg-OH, manufactured by BACHEM) and 20 mM $CaCl_2$, and a reaction was then initiated at 37° C. Ten and twenty minutes after initiation of the reaction, 100 μL of the reaction solution was sampled, and was then added to 200 μL of 25 mM citric acid solution to prepare a reaction stop solution. To this reaction stop solution, 1 mL of ethyl acetate was added, and then, the mixed solution was stirred for 10 seconds and was then centrifuged (12000×g, 10 minutes), so that an ethyl acetate layer was recovered as a supernatant. The absorbance of the recovered ethyl acetate layer as a supernatant at 320 nm was measured, so that the amount of Pz-Pro-Leu released by collagenase was obtained. The enzyme activity was evaluated by calculating the rate of generating Pz-Pro-Leu per minute from the amounts of Pz-Pro-Leu generated 10 minutes and 20 minutes later. The amount of enzyme that decomposes 1 μmol Pz peptide (releases 1 μmol Pz-Pro-Leu) per minute was defined as 1 U.

Collagenase Activity

Collagenase activity was measured using PROTAZYME OL TABLETS (manufactured by Megazyme). A substrate solution (300 μL) prepared by suspending 1 OL tablet in a 200 mM Tris buffer containing 10 mM $CaCl_2$ was dispensed in a 1.5 mL tube, while stirring, and it was then placed on ice. Into the dispensed substrate solution, 100 μL of the enzyme solution was added and mixed, and the mixed solution was then stirred using BioShaker set at 40° C. for 30 minutes, so as to perform a reaction. Thirty minutes after the reaction, 1 mL of 2% trisodium phosphate solution was added to the reaction mixture to terminate the enzyme reaction, and the reaction mixture was then centrifuged (13000 g, 10 minutes). The supernatant (200 μL) was transferred into a microtiter plate, and the absorbance at 590 nm was then measured. The intensity of the collagenase activity was determined based on the value at 590 nm that was increased for 30 minutes.

Casein-Decomposing Activity

Casein-decomposing activity was measured using PROTAZYME AK TABLETS (manufactured by Megazyme). A substrate solution (300 μL) prepared by suspending 1 AK tablet in a 200 mM Tris buffer containing 10 mM $CaCl_2$ was dispensed in a 1.5 mL tube, while stirring, and it was then placed on ice. Into the dispensed substrate solution, 100 μL of the enzyme solution was added and mixed, and the mixed solution was then stirred using BioShaker set at 40° C. for 30 minutes, so as to perform a reaction. Thirty minutes after the reaction, 1 mL of 2% trisodium phosphate solution was added to the reaction mixture to terminate the enzyme reaction, and the reaction mixture was then centrifuged (13000 g, 10 minutes). The supernatant (200 μL) was transferred into a microtiter plate, and the absorbance at 590 nm was then measured. The intensity of casein-decomposing activity was determined based on the value at 590 nm that was increased for 30 minutes.

Confirmation of CTP-Producing Ability

A serially diluted enzyme solution was allowed to react with gelatin (gelatin with a final concentration of 2%) for 12 hours, and thereafter, the reaction mixture was boiled for 10 minutes to terminate the reaction. This reaction stop solution was 10-fold diluted with ultrapure water, and was then subjected to gel filtration analysis using Superdex peptide 7.5/300, so that the amount of CTP generated was confirmed. Conditions for the gel filtration were as follows.

Superdex_peptide 7.5/300
Buffer: 0.02 M Phosphate buffer containing 0.25 M NaCl, pH 7
Flow rate: 0.28 mL/min
Applied amount: 100 μL
Detection: 214 nm
System: AKTA/low-temperature storage 5. Enzymatic Properties of 57413 Strain Collagenase (1) Optimal Temperature The influence of the temperature on the reactivity of the present enzyme was confirmed. A measurement method using Pz-peptide as a substrate was applied, and the activity was measured, while the temperature upon the reaction was changed from 30° C. to 60° C. The optimal temperature was evaluated using relative activity obtained when the maximum activity (the highest value of the activity) was set at 100%. As shown in FIG. 2, the optimal temperature was around 40° C.

(2) Temperature Stability

The temperature stability of the present enzyme was examined. A sample prepared by 5-fold diluting the present enzyme solution with a 200 mM Tris-HCl buffer containing 20 mM $CaCl_2$ was treated at each temperature (0° C., 30° C., 40° C., 50° C., and 60° C.) for 30 minutes. Thereafter, the activity was measured by a measurement method using Pz-peptide as a substrate. As shown in FIG. 3, it was found that the activity was not decreased from the treatment at 0° C. (on ice) to the treatment at 40° C., and thus that the activity was stable until 40° C.

(3) Optimal pH

The influence of pH on the reactivity of the present enzyme was examined. As a buffer for dissolving Pz-peptide, each 200 mM buffer containing 20 mM $CaCl_2$ was used (wherein an acetate buffer was used at pH 4, 5 or 6; a PIPES buffer was used at pH 6 or 7; a Tris-HCl buffer was used at pH 7, 8 or 9; and a glycine buffer was used at pH 9, 10 or 11), instead of the 200 mM Tris-HCl buffer containing 20 mM $CaCl_2$. Thereafter, the activity was measured. The optimal pH was evaluated using relative activity obtained when the maximum activity was set at 100%. As shown in FIG. 4, the optimal pH was found to be around pH 7.

(4) pH Stability

The pH stability of the present enzyme was examined. The present enzyme solution was 5-fold diluted with each 200 mM buffer containing 20 mM $CaCl_2$ (wherein an acetate buffer was used at pH 4, 5 or 6; a PIPES buffer was used at pH 6 or 7; a Tris-HCl buffer was used at pH 7, 8 or 9; and a glycine buffer was used at pH 9, 10 or 11), and the diluted solution was then treated at 30° C. for 30 minutes. Thereafter, the activity was measured by a measurement method using Pz-peptide as a substrate. The pH stability was evaluated, using relative activity to the enzyme activity that was set at 100% when the enzyme solution was 5-fold diluted with 200 mM Tris-HCl buffer containing 20 mM $CaCl_2$ (pH 7) and was then stored at 0° C. (on ice). As shown in FIG. 5, it was found that high activity (85% or more) was maintained in the pH range from about 5 to about 9.5, and that the enzyme was stable in this pH range.

6. Low-Temperature Reactivity of Collagenase

Method

With regard to the above-described 57413 strain collagenase (the enzyme of the present invention) and *Streptomyces*-derived collagenase for comparative use, low-temperature reactivity was measured. Collagenase activity was measured using PROTAZYME OL TABLETS (manufactured by Megazyme; substrate: AZCL-collagen). A substrate solution (150 µL) prepared by suspending 1 OL tablet in a 200 mM Tris buffer containing 10 mM $CaCl_2$ was dispensed in a 1.5 mL tube, while stirring, and it was then placed on ice. Into the dispensed substrate solution, 50 µL of the enzyme solution was added and mixed, and the mixed solution was then stirred using BioShaker set at a predetermined temperature, so as to perform a reaction. The reaction was terminated by adding 500 µL of 2% trisodium phosphate solution to the reaction mixture, and the reaction mixture was then centrifuged (13000 g, 10 minutes). The supernatant (200 µL) was transferred into a microtiter plate, and the absorbance at 590 nm was then measured. The intensity of the collagenase activity was evaluated based on an increase in the absorbance at 590 nm.

Results

The results are shown in Table 1 and FIG. 6. The relative activity of the collagenase of the present invention at 20° C. to 30° C. was higher than that of the comparative enzyme.

TABLE 1

| Sample | Reaction temperature [° C.] | Relative activity [%] |
|---|---|---|
| Enzyme of the present invention | 40 | 100.0 |
| | 30 | 41.0 |
| | 20 | 10.6 |
| | 4 | 1.0 |
| Comparative enzyme | 40 | 100.0 |
| | 30 | 26.0 |
| | 20 | 8.1 |
| | 4 | 1.2 |

7. Confirmation of Ability to Generate Collagen Tripeptide

Method

Using the 57413 strain collagenase (the enzyme of the present invention) and *Streptomyces*-derived collagenase for comparative use, the following experiment was carried out.

Method of Measuring Natural Collagen-Decomposing Activity

The enzyme solution (0.1 mL) was added to 5 mL of 50 mM TES buffer (pH 7.4) containing 25 mg of bovine Achilles tendon-derived insoluble type I collagen (manufactured by Sigma) and 0.36 mM $CaCl_2$, and the mixed solution was then reacted at 37° C. for 5 hours. Thereafter, the reaction solution was filtrated through a filter. To 100 µL of the filtrate, 1 mL of ninhydrin reagent containing 0.1 M citric acid (pH 5.0) was added, and thereafter, the obtained mixture was heated at 100° C. for 20 minutes and was then cooled. After that, 5 mL of 50% 1-propanol was added to the reaction mixture, and an increase in the absorbance at 570 nm was then measured. 1 Collagen degrading unit (CDU) was defined to be the amount of enzyme, in which a peptide corresponding to 1.0 µmol leucine is released from collagen when incubated in the presence of Ca ions at 37° C. at pH 7.4 for 5 hours.

Confirmation of Generation of Collagen Tripeptide

A serially diluted enzyme solution was allowed to react with 5% fish gelatin type A (manufactured by NITTA GELATIN INC.) for 20 hours, and thereafter, the reaction mixture was boiled for 10 minutes to terminate the reaction. This reaction stop solution was 4-fold diluted with ethanol, and a precipitate was then removed by centrifugation. Thereafter, the supernatant was diluted with ultrapure water to a concentration of 50 ppm relative to gelatin, and was then treated with MF (0.45 µm). After that, the resultant was subjected to an LC-MS analysis, so that the peak areas of Gly-Pro-Hyp, Gly-Pro-Ala, and Gly-Glu-Arg were evaluated among CTPs. The CTP-producing ability of the present enzyme was compared with that of *Streptomyces*-derived collagenase.

(LC-MS analysis)
Column: TSK gel ODS-80TM, 150 mm
Solvent: ultrapure water+0.1% formic acid
Flow rate: 1 mL/min
Amount injected: 1 µL
Detection: Positive ion mode, SIM method Results The results are shown in FIG. 7 to FIG. 9.

It was found that the present enzyme generates Gly-Pro-Hyp and Gly-Pro-Ala in amounts equivalent to those generated by *Streptomyces*-derived collagenase, and further that the ability of the present enzyme to generate Gly-Glu-Arg is superior to that of *Streptomyces*-derived collagenase.

8. Confirmation of Meat-Tenderizing Effect

Using the 57413 strain collagenase (the enzyme of the present invention) and *Streptomyces*-derived collagenase for comparative use, the following experiment was carried out.

8-1. Effect of Tenderizing Pork Ribs

Method 13.5 mL of pickle liquid (1.5 w/v % common salt, 1.5 w/v % sodium bicarbonate, and 0.7 w/v % calcium lactate) containing 30 CDU/mL collagenase was randomly injected into 140 g of pork ribs, and the pork ribs were then kneaded by hand. Thereafter the pork ribs were preserved in a low-temperature storage (about 5° C.) for 3 days. Thereafter, the pork ribs were divided into 4 portions, which were then treated in a hot water bath for 10 minutes. After that, the meats were divided into fatty meats and lean meats, and both of the meats were then evaluated in terms of physical properties, using RHEO METER (manufactured by Sun Scientific Co., Ltd.). The results obtained by measuring the load at a depth of 3 mm are shown below. As the load value decreases, it means that the meats are soft.

Results

The results are shown in FIG. 10.

It was revealed that, differing from the *Streptomyces*-derived collagenase, the present enzyme has the effect of tenderizing fatty meats, without tendering lean meats.

8-2. Effect of Tenderizing Beef Chuck Eye Roll

Method

The tendon of beef chuck eye roll was cut into a 1 cm square cube, which was then immersed in 30 mL of the enzyme solution (30 CDU/mL) and was then treated in a low-temperature storage (about 5° C.) for 3 days. After completion of the treatment, the resultant was not heated, and was directly evaluated using RHEO METER, in terms of physical properties (breaking strength and load at a depth of 3 mm). Both the breaking strength and the load are used as indicators of the tenderization degree. As the values decrease, it means that the meats are soft.

Results

The results are shown in FIG. 11.

It was revealed that the present enzyme has low breaking strength and low load, compared with the *Streptomyces*-derived collagenase, and that the present enzyme has the effect of allowing the tendons of beef chuck eye roll to be easily bitten off and tenderizing the tendons of the beef chuck eye roll.

INDUSTRIAL APPLICABILITY

The enzyme agent of the present invention comprises, as an active ingredient, collagenase derived from highly safe microorganisms. Accordingly, the enzyme agent of the present invention is suitable for the use in the field of food products or medical purposes, and thus, the present enzyme agent is industrially highly valuable.

The present invention is not limited to the above-described embodiments and examples of the invention in any way. The present invention includes various modifications that can be easily conceived of by a person skilled in the art without departing from the scope of claims. The contents of the study papers, published patent publications, patent publications, and the like that are explicitly specified in the present description shall be cited by incorporating the entire contents thereof.

SEQUENCE LISTING FREE TEXT

SEQ ID NO: 5: explanation of artificial sequence: forward primer

SEQ ID NO: 6: explanation of artificial sequence: reverse primer

The invention claimed is:

1. A method for producing a collagen tripeptide, comprising:

allowing an enzyme agent to act on collagen or gelatin; and producing collagen tripeptides comprising Gly-Glu-Arg, wherein the enzyme agent comprises, as an active ingredient, an active collagenase having the amino acid sequence of SEQ ID NO: 1.

2. The method according to claim 1, wherein the active collagenase is derived from *Lysinibacillus fusiformis*.

3. The method according to claim 1, wherein the collagen tripeptides further comprise Gly-Pro-Hyp and Gly-Pro-Ala.

4. The method according to claim 1, wherein the enzyme agent is for use in production of a collagen tripeptide.

5. The method according to claim 1, wherein the enzyme agent is for use in tenderization of edible meat.

* * * * *